United States Patent
Liao et al.

(12) 
(10) Patent No.: US 12,090,207 B2
(45) Date of Patent: Sep. 17, 2024

(54) DRUG DELIVERY COMPOSITION, METHOD FORMING THE SAME AND METHOD FOR TREATING INNER EAR DISORDERS

(71) Applicants: National Taiwan University of Science and Technology, Taipei (TW); National Defense Medical Center, Taipei (TW)

(72) Inventors: Ai-Ho Liao, Taipei (TW); Chih-Hung Wang, New Taipei (TW); Cheng-Ping Shih, Taipei (TW)

(73) Assignees: National Taiwan University of Science and Technology, Taipei (TW); National Defense Medical Center, Taipei (TW)

( * ) Notice: Subject to any disclaimer, the term of this patent is extended or adjusted under 35 U.S.C. 154(b) by 0 days.

(21) Appl. No.: 17/379,986

(22) Filed: Jul. 19, 2021

(65) Prior Publication Data
US 2022/0273799 A1 Sep. 1, 2022

(30) Foreign Application Priority Data
Feb. 26, 2021 (TW) .................... 110106924

(51) Int. Cl.
| | |
|---|---|
| A61K 47/34 | (2017.01) |
| A61K 9/10 | (2006.01) |
| A61K 45/06 | (2006.01) |
| A61K 47/02 | (2006.01) |
| A61K 47/42 | (2017.01) |

(52) U.S. Cl.
CPC .............. *A61K 47/34* (2013.01); *A61K 9/10* (2013.01); *A61K 45/06* (2013.01); *A61K 47/02* (2013.01); *A61K 47/42* (2013.01)

(58) Field of Classification Search
CPC .......... A61K 47/34; A61K 47/10; A61K 9/10; A61K 47/42
See application file for complete search history.

(56) References Cited

U.S. PATENT DOCUMENTS

| | | | |
|---|---|---|---|
| 9,486,405 B2 | 11/2016 | Piu et al. | |
| 2013/0041311 A1 | 2/2013 | Kohane et al. | |
| 2015/0056273 A1* | 2/2015 | Liao ...................... | A61K 47/42 424/450 |
| 2017/0027930 A1 | 2/2017 | Piu et al. | |

FOREIGN PATENT DOCUMENTS

| | | |
|---|---|---|
| EP | 2490722 A2 | 8/2012 |
| EP | 1928405 B1 | 9/2014 |
| TW | 201429492 A | 8/2014 |
| WO | 2014039781 A1 | 3/2014 |

OTHER PUBLICATIONS

Cheng-Ping Shih, "The Study of Ultrasound-aided Microbubbles in Facilitating the Delivery of Drugs to the Inner Ear via the Round Window Membrane", Doctorate Dissertation of Graduate Institute of Medical Science, National Defense Medical Center, Taipei, Taiwan R.O.C., Aug. 26, 2017 1-50.
Lanmei Li et al., "Review of Curcumin Physicochemical Targeting Delivery System", International Journal of Nanomedicine, Dec. 7, 2020, 9799-9821.
Liao Ai-Ho et al., "Ultrasound-induced microbubble cavitation via a transcanal or transcranial approach facilitates inner ear drug delivery." JCI Insight, Feb. 13, 2020, 5(3):e132880, doi: 10.1172/jci.insight.132880.
Shih Cheng-Ping et al., "Middle-ear dexamethasone delivery via ultrasound microbubbles attenuates noise-induced hearing loss." Laryngoscope, Dec. 27, 2018, doi: 10.1002/lary.27713. [Epub ahead of print] PubMed PMID: 30588634.
Shih Cheng-Ping et al., "Ultrasound-aided microbubbles facilitate the delivery of drugs to the inner ear via the round window membrane", Journal of Controled Release, Apr. 28, 2013, 167(2):167-174.
Liao Ai-Ho et al., " Effectiveness of a layer-by-layer microbubbles-based delivery system for applying minoxidil to enhance hair growth", Theranostics, Apr. 11, 2016, 6(6): p. 817-827.
Heskin M. et al., "Solution properties of poly(N-isopropylacrylamide)", Journal of Macromolecular Science, Dec. 1968, 2:pp. 1441-1455.
Dhara D., et al., "Phase transition in linear and cross-linked poly(N-isopropylacrylamide) in water: effect of various types of additives", Journal of Macromolecular Science, Rev. Macromol. Chem. Phys., 2000,C40:pp. 51-68.
Bae YH et al., "Thermo-sensitive polymers as on-off switches for drug release". Makromol. Chem. Rapid Commun., May 4, 1987,8:pp. 481-485.
Kang Derwent J. et al., "Thermoresponsive Hydrogels as a New Ocular Drug Delivery Platform to the Posterior Segment of the Eye",. Trans. Am. Ophthalmol. Soc., 2008, vol. 106, pp. 206-213.
Moghimi SM et al., "Poloxamers and poloxamines in nanoparticle engineeringand experimental medicine", [J]. Trends Biotechnol, Oct. 2000, vol. 18: pp. 412-420.
Jackson JK., et al., "Neutrophil activation by plasma opsonized polymeric microspheres: inhibitory effect of Pluronic F127", Biomaterials, Oct. 2000, 21: pp. 1483-1491.
Ai-Ho Liao, et al., "Development of thermosensitive poloxamer 407-based microbubble gel with ultrasound mediation jor inner ear drug delivery", Drug Delivery, May 31, 2021, vol. 28, No. 1, pp. 1256-1271.
Karsten Mader et al., Controlled drug release to the inner ear: Concepts, materials, mechanisms, and performance:, Hearing Research, Mar. 9, 2018, pp. 49-66.
Hongzhou Liu et al., "Current strategies for drug delivery to the inner ear", Acta Pharmaceutica Sinica B, Feb. 3, 2013, pp. 86-96.
Besty Szeto MPH et al., "Inner ear delivery: Challenges and opportunities", Laryngoscope Investigative Otolaryngology, 2020;5:pp. 122-131.

(Continued)

*Primary Examiner* — Shobha Kantamneni
(74) *Attorney, Agent, or Firm* — CKC & Partners Co., LLC

(57) ABSTRACT

The disclosure provides a drug delivery composition, method of forming the same and method for treating inner ear disorders. The drug delivery composition includes a temperature sensitive hydrogel, a plurality of microbubbles and a drug. Every microbubble has a protein shell and an inert gas core. These microbubbles are dispersed in the temperature sensitive hydrogel. The drug is dispersed in the temperature sensitive hydrogel. Moreover, the drug delivery composition has a viscosity that can induce cavitation effect.

18 Claims, 17 Drawing Sheets

(56) References Cited

OTHER PUBLICATIONS

Matthew Ku et al., "An extended release ciprofloxacin/dexamethasone hydrogel for otitis media", International Journal of Pediatric Otorhinolaryngology, Aug. 18, 2020.

Julia Clara Gausterer et al., "Intratympanic application of poloxamer 407 hydrogels result in sustained N-acetylcysteine delivery to the inner ear", European Journal of Pharmaceutics and Biopharmaceutics, Mar. 13, 2020, pp. 143-155.

Vibhuti Agrahari et al., "Inner ear targeted drug delivery: what does the future hold?", Therapeutic delivery, Apr. 2017, pp. 179-184.

Dan Zhao et al., "Novel facile thermosensitive hydrogel as sustained and controllable gene release vehicle for breast cancer treatment", European Journal of Pharmaceutical Science, Mar. 26, 2019, pp. 145-152.

Tomas Gonzalez-Fernandez et al., "Gene Delivery of TGF-β3 and BMP2 in an MSC-Laden Alginate Hydrogel for Articular Cartilage and Endochondral Bone Tissue Engineering", Tissue Engineering: Part A, vol. 22, May 5, 2016, pp. 776-787.

Minh Khanh Nguyen et al., "Covalently tethering siRNA to hydrogels for localized, controlled release and gene silencing", Science Advances, Aug. 28, 2019.

Young-Min Kim et al., "Targetable micelleplex hydrogel for long-term, effective, and systemic siRNA delivery", Biomaterials, Jun. 18, 2014, pp. 7970-7977.

Ai-Ho Liao et al., "Development of thermosensitive poloxamer 407 based microbubble gel for ultrasound mediated middle ear drug delivery", Drug Deliv. Dec. 2021;28(1):1256-1271.

Ming-Wei Li, "Ultrasound mediated microbubble smart gel cavitation for inner ear drug delivery", Thesis submitted to the Graduate Institute of Mechatronic Engineering, National Taipei University of Technology, Taiwan, R.O.C., Jul. 2020.

\* cited by examiner

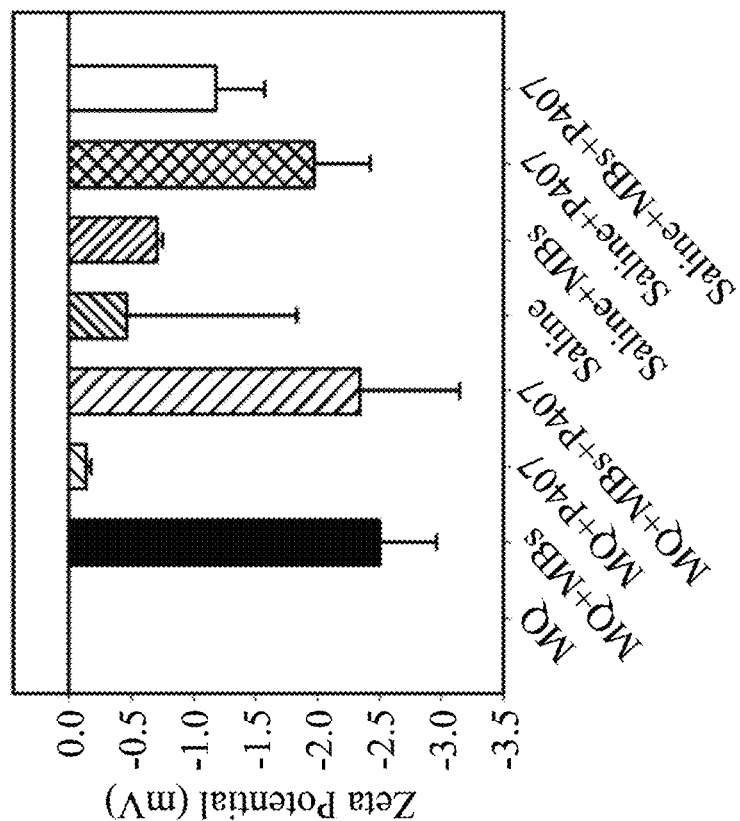
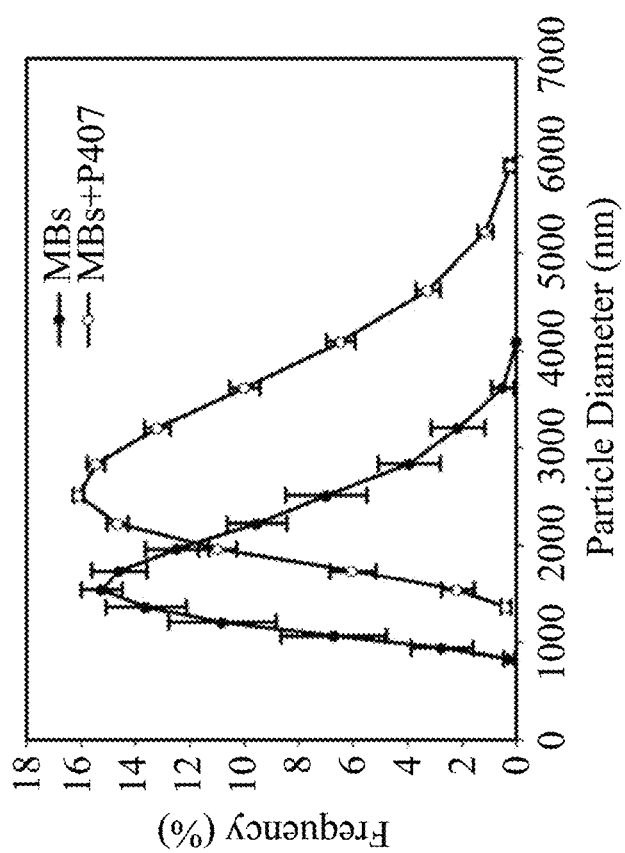
Fig. 3A
Fig. 3B

DRUG DELIVERY COMPOSITION, METHOD FORMING THE SAME AND METHOD FOR TREATING INNER EAR DISORDERS

CROSS-REFERENCE TO RELATED APPLICATION

This application claims priority to Taiwan Application Serial Number 110106924, filed on Feb. 26, 2021, which is herein incorporated by reference in its entirety.

BACKGROUND

Field of Invention

The present disclosure relates to a drug delivery composition. More particularly, the present disclosure relates to a drug delivery composition used in the ears, method forming the same and method for treating inner ear disorders.

Description of Related Art

The World Health Organization (WHO) estimated in 2019 that 466 million people worldwide had hearing loss (6.1% of the World's population), and the unsolved hearing loss cost the global economy USD 750 billion every year. Therefore, the inconvenience caused by sensory organ damage is bound to affect everyone's quality of life.

In the treatment of diseases of the inner ear, systemic administration must pass through the blood labyrinth barrier (BLB) to reach the inner ear. Since only a small amount of drugs can penetrate the labyrinth barrier to the inner ear, a high dose of drugs must be used throughout the body in order to obtain the appropriate concentration in the inner ear for therapeutic effect. In addition, systemic administration of high concentrations of drugs may cause many side effects. For example, systemic administration of steroids at high concentrations may cause complications such as hyperglycemia, hypertension, gastrointestinal bleeding, and necrosis of the joints.

Therefore, for the treatment of inner ear diseases, novel methods are needed to avoid systemic high dose administration.

SUMMARY

In some embodiments of the present disclosure, the present disclosure provides a drug delivery composition, including a temperature-sensitive hydrogel, a plurality of microbubbles and a drug. Each of these microbubbles has a protein shell and an inert gas core, and these microbubbles are dispersed in the temperature-sensitive hydrogel. The drug delivery composition appears liquid at low temperature, with low viscosity, and can produce cavitation effect spontaneously or in combination with ultrasound or other forms of energy. As such, the opening permeability of cells or tissues can be enhanced. The drug is dispersed in the temperature-sensitive hydrogel. And, the drug delivery composition has a viscosity for inducing cavitation effect. The aforementioned viscosity can increase with the increase of temperature, so the drug delivery composition forms a gel state when the temperature increases.

In some embodiments of the present disclosure, the viscosity for inducing cavitation effect is from about 0.01 Pa·S to about 5.5 Pa·S.

In some embodiments of the present disclosure, a total weight of the drug delivery composition is 100 percentage by weight. Then, a content of the temperature-sensitive hydrogel is from about 8 percentage by weight to about 15 percentage by weight. A content of these microbubbles is from about 1 percentage by weight to about 10 percentage by weight, and an amount of these microbubbles in per mL of the drug delivery composition is from about $1\times10^8$ to about $2\times10^{10}$.

In some embodiments of the present disclosure, a particle diameter of each of these microbubbles is from about 0.5 μm to about 3.7 μm.

In some embodiments of the present disclosure, the drug includes steroid, anti-apoptotic drug, neurotrophic factor, growth factor, antibiotic, antioxidant, or a combination thereof.

In some embodiments of the present disclosure, the temperature-sensitive hydrogel includes a poloxamer.

In some embodiments of the present disclosure, the poloxamer includes polyoxyethylene-polyoxypropylene copolymer.

In some embodiments of the present disclosure, the present disclosure provides a method for treating inner ear disorders, and the method includes administering to the subject in need thereof an effective amount of the aforementioned drug delivery composition.

In some embodiments of the present disclosure, the present disclosure provides a method of manufacturing a drug delivery composition, and the method includes the following steps. A microbubble material and a first solvent are mixed to form a first mixture. The first mixture is treated with an ultrasonic wave for about 100 seconds to 140 seconds to form a plurality of microbubbles. Each of these microbubbles has a protein shell and an inert gas core. A drug and a second solvent are mixed to form a second mixture. The second mixture and a temperature-sensitive hydrogel are mixed to form a temperature-sensitive drug hydrogel. These microbubbles and the temperature-sensitive drug hydrogel are mixed to form the drug delivery composition.

In some embodiments of the present disclosure, a viscosity of the drug delivery composition is from about 0.01 Pa·S to about 5.5 Pa·S.

In some embodiments of the present disclosure, the first solvent comprises saline.

In some embodiments of the present disclosure, the second solvent comprises dimethyl sulfoxide.

In some embodiments of the present disclosure, a total weight of the drug delivery composition is 100 percentage by weight. Then, a content of the temperature-sensitive hydrogel is from about 8 percentage by weight to about 15 percentage by weight. A content of these microbubbles is from about 1 percentage by weight to about 10 percentage by weight, and an amount of these microbubbles of the drug delivery composition is from about $1\times10^8$ to about $2\times10^{10}$ per mL.

In some embodiments of the present disclosure, a particle diameter of each of these microbubbles is from about 0.5 μm to about 3.7 μm.

In some embodiments of the present disclosure, the drug includes steroid, anti-apoptotic drug, neurotrophic factor, growth factor, antibiotic, antioxidant, or a combination thereof.

In some embodiments of the present disclosure, the temperature-sensitive hydrogel includes a poloxamer.

In some embodiments of the present disclosure, the poloxamer includes polyoxyethylene-polyoxypropylene copolymer.

It is to be understood that both the foregoing general description and the following detailed description are by examples, and are intended to provide further explanation of the present disclosure as claimed.

BRIEF DESCRIPTION OF THE DRAWINGS

The present disclosure can be more fully understood by reading the following detailed description of the embodiment, with reference made to the accompanying drawings as follows. It should be understood that, according to industry practice, the various features are not drawn to scale. In fact, for the sake of clarity, the size of the various features can be arbitrarily increased or decreased. It should be noted that, the wording "DEX" in all figures means dexamethasone.

FIG. 3A is a particle diameter curve diagram of the microbubbles and the microbubbles after mixing with the temperature-sensitive hydrogel according to some embodiments of the present disclosure.

FIG. 3B is a zeta potential analysis diagram of the microbubbles and the microbubbles after mixing with the temperature-sensitive hydrogel according to some embodiments of the present disclosure.

DETAILED DESCRIPTION

Figure 1:
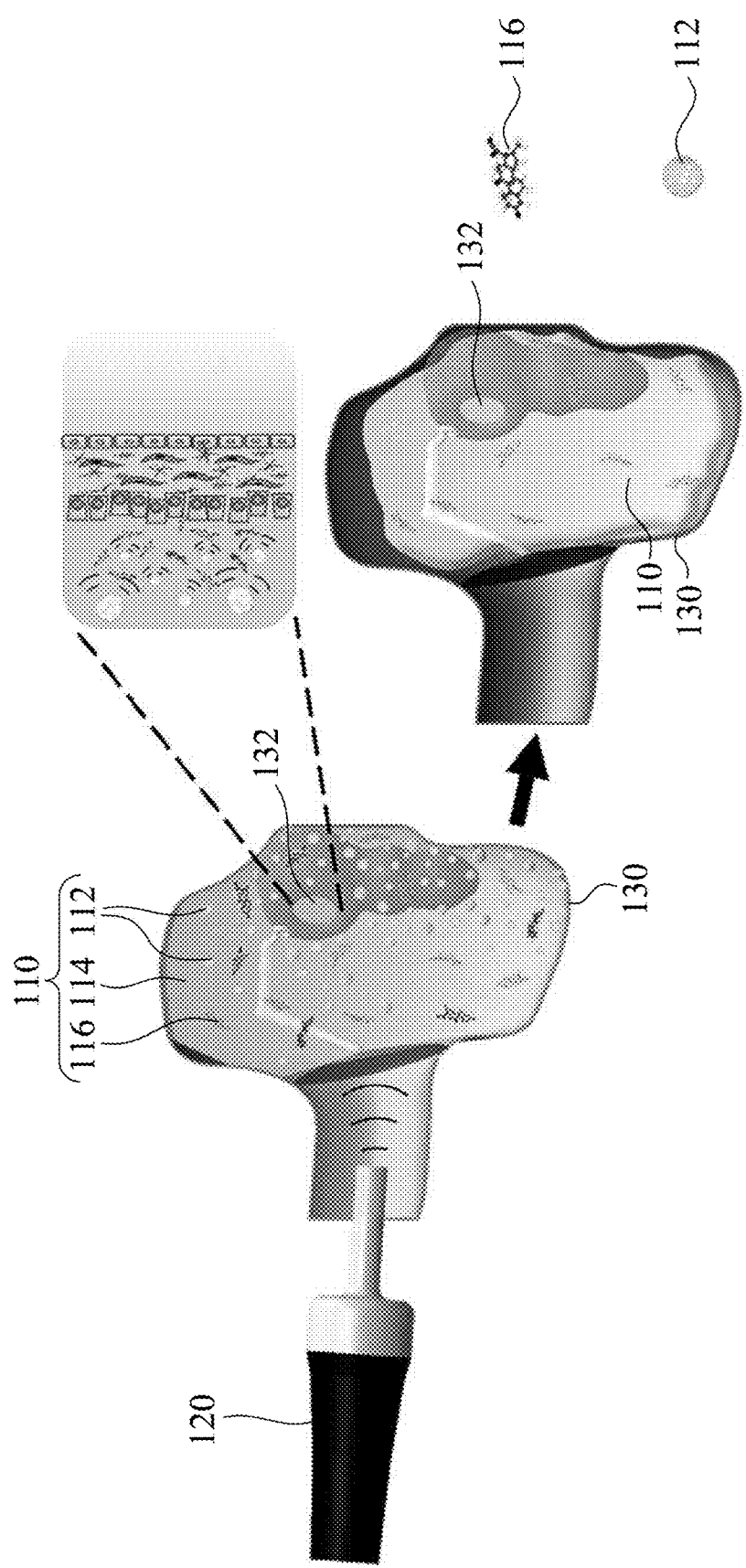
FIG. 1 is a delivery schematic diagram of the drug delivery composition with ultrasound according to some embodiments of the present disclosure.

For the purpose of making the present disclosure more detailed and complete, the following paragraphs describe embodiments and specific examples in detail. However, this is not the only form in which embodiments of the present disclosure are exercised or applied. The embodiments revealed below may be combined or substituted for one another, or may be appended to one embodiment without further record or description.

The words "contain", "include", "have" and similar terms used in this document indicate the features, areas, integers, steps, operations, elements and/or components recorded therein, but do not exclude other features, areas, integers, steps, operations, elements, components, and/or a combination thereof.

The drug delivery composition of the present disclosure could spontaneously produce cavitation effect in liquid form. Or, the drug delivery composition in liquid form could be combined with ultrasonic wave or other forms of energy to produce cavitation effect. The cavitation effect would increase cells or tissues permeability. And, the drug delivery composition would form a gel form with rising temperature. In this way, the efficiency of drug delivery could be improved in a short period of time and the purpose of long-lasting stay and sustained release could be achieved, as well as the effect of in-situ treatment.

Preparation: Take the preparation of a temperature-sensitive microbubbles drug hydrogel with 2% dexamethasone (herein after DEX) and 12.5% poloxamer 407 as an example.

(1) Preparation of microbubbles: 132 mg/0.66 mL of human serum albumin is mixed with 9.34 mL of saline (pH 7.4, 0.9% NaCl) containing $C_3H_8$ gas to form 10 mL of microbubbles mixture. Then, the 10 mL microbubbles mixture is ultrasonically treated with a cell processor for 2 minutes to obtain the microbubbles (hereinafter MB) mixture with albumin shell.

(2) Preparation of temperature-sensitive hydrogel: 15.63 g of poloxamer 407 (hereinafter P407) was dissolved in 84.37 mL of saline and stirred at 600 rpm at 4° C. for 30 min to obtain temperature-sensitive hydrogel solution of 15.63% of P407. It is important to note that the concentration of the P407 temperature-sensitive hydrogel prepared in this step is only one of the embodiments in the present disclosure. In subsequent embodiments, other P407 temperature-sensitive hydrogels with different concentrations will also be prepared in the same manner as described in this step.

In some embodiments, the temperature-sensitive hydrogel used in the present disclosure includes amphiphilic triblock copolymer, or N-isopropylacrylamide (NIPAAm), and ionic polymers includes polysaccharide containing at least one carboxylic acid. The aforementioned amphiphilic triblock copolymer includes poloxamer. Poloxamer is composed of polyethylene oxide-polypropylene oxide-polyethylene oxide (PEO-PPO-PEO). In which, polysaccharides of at least one carboxylic acid group contain mannuronic acid and guluronic acid.

In some embodiments, the temperature-sensitive hydrogel used in the present disclosure includes poloxamer. Poloxamer is a non-ionic triblock copolymer consisting of an intermediate hydrophobic polyoxypropylene chain flanking two segments of hydrophilic polyoxyethylene. Poloxamer can be used to evaluate various drug delivery applications, and can demonstrate sensitivity to chemotherapeutic resistance to cancer. Due to the prescribable length of the polymers, the properties of the poloxamer vary slightly. Usually, this copolymer uses the letter "P" (poloxamer) with three digits as its common name. The first two digits×100 is the approximate molecular mass of middle section of the polyoxypropylene, and the last digit×10 is the percentage of polyoxyethylene (such as P407 means that the molecular weight of polyoxypropylene is 4000 g/mol, and the percentage of polyoxyethylene is 70%).

(3) Preparation of temperature-sensitive drug hydrogel: 200 mg of DEX was dissolved in 1 mL of 99.7% dimethyl sulfoxide (hereafter referred to as DMSO) to form DEX solution. Then, 0.1 mL of the aforementioned DEX solution was added to 0.8 mL of 15.63% P407 temperature-sensitive hydrogel solution to form 0.9 mL of DEX-P407 solution. Finally, triethanolamine (2, 2', 2"-nitrilotriethanol) was used to adjust the pH value of Dex-P407 solution to 7.

In some embodiments, the drugs could be collocated with the present disclosure includes, but not limited to, steroid, anti-apoptotic drug, neurotrophic factor, growth factor, antibiotic, antioxidant or a combination thereof. Growth factor includes, but not limited to, epidermal growth factor (EGF), ephrins, erythropoietin (EPO), fibroblast growth factor (FGF), insulin-like growth factors (IGF), interleukins, neurotrophins and vascular endothelial growth factor (VEGF).

(4) Preparation of temperature-sensitive microbubbles drug hydrogel: 0.1 mL of microbubbles mixture was mixed with 0.9 mL DEX-P407 solution to obtain a temperature-sensitive microbubble drug hydrogel (i.e., the drug delivery composition described in the present disclosure). The 10 mL of temperature-sensitive microbubble drug hydrogel contained 2% DEX, 12.5% P407 and 10% microbubbles, among which the density of microbubbles in each mL of t temperature-sensitive microbubble drug hydrogel was $4.2 \times 10^8$.

It should be noted that the preparation cases are intended to reveal the order of addition and the background environment at the time when manufacturing. Thus, the preparation cases are based on the preparation of a 2% DEX-12.5% P407 temperature-sensitive microbubbles drug hydrogel.

Other concentration combinations are prepared in the same manner as the present preparation, and their contents and efficacy are described in the following embodiments.

One of the main purposes of the present disclosure is to achieve long-term and stable drug release in the affected area when treating inner ear disorders, and simultaneously promote the permeability of the round window membrane. Thus, the efficiency of drug delivery into the body would be increased. In order to have a more complete understanding of the present disclosure, please refer to FIG. 1. FIG. 1 is a delivery schematic diagram of the drug delivery composition with ultrasound according to some embodiments of the present disclosure. The drug delivery composition 110, containing microbubbles 112, temperature-sensitive hydrogel 114 and drug 116, is injected into the middle ear cavity 130. When the ultrasonic device 120 carries out ultrasonic treatment on the drug delivery composition 110 located in the middle ear cavity 130, the microbubbles 112 would produce cavitation effect, thus forming jet flow and physical effect on the round window membrane 132. According to the ultrasonic intensity applied to the microbubbles 112, the cavitation effect can be divided into steady state cavitation effect and inertia cavitation effect. The steady-state cavitation effect produces microflow in adjacent cells, and improves the permeability of the cell membrane (round window membrane 132). The inertial cavitation effect causes the microbubbles 112 to burst and cause a jet flow into the cell membrane (round window membrane 132), and form a temporary hole in the cell membrane (round window membrane 132). After the ultrasonic treatment, the temperature-sensitive hydrogel 114 in the drug delivery composition 110 will gradually develop colloidal properties and remain in situ under the influence of human body temperature. Thus, the drug delivery composition would achieve a long-term and stable drug release, and the efficiency of drug delivered into the body would be increase.

Figure 2:
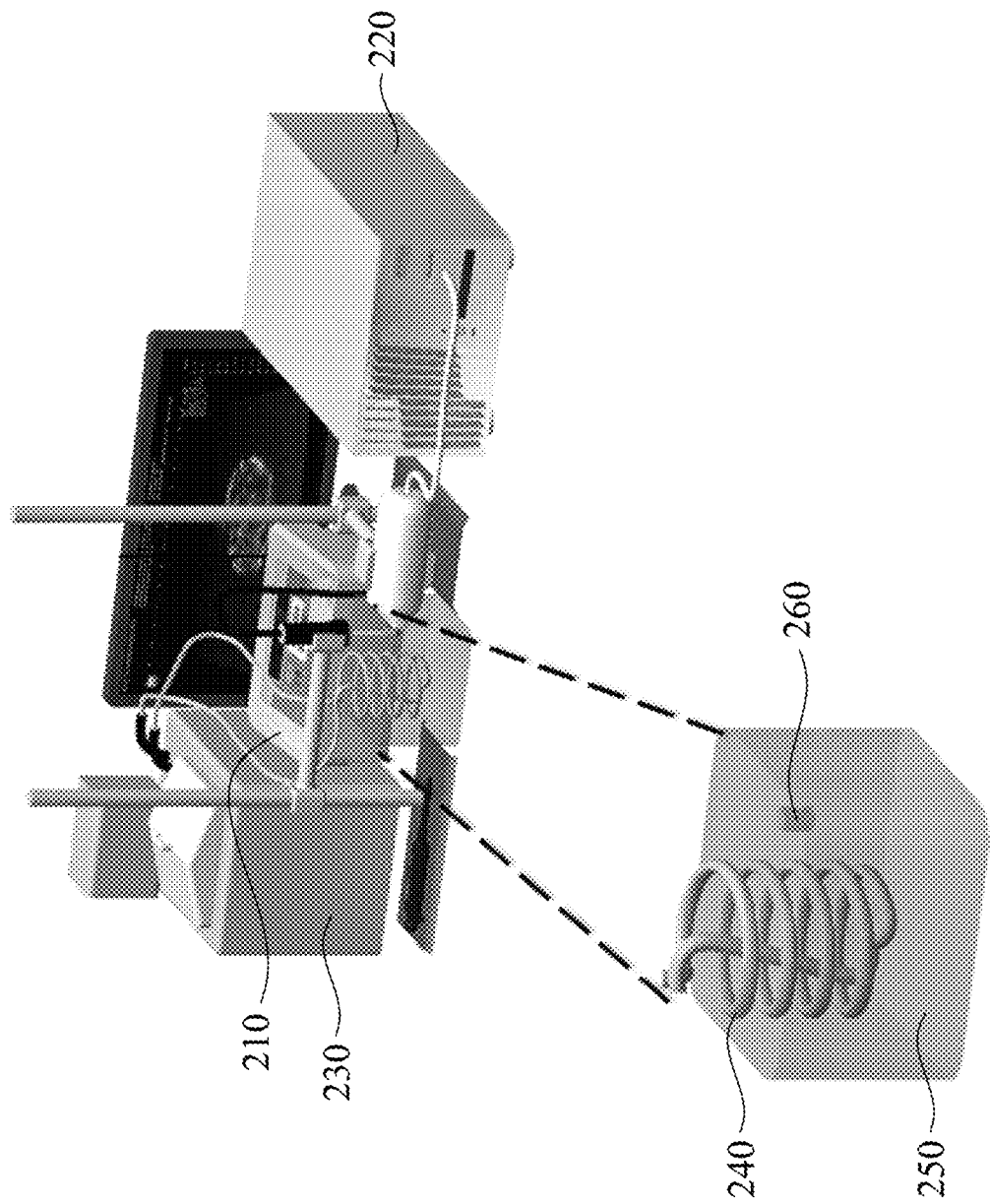
FIG. 2 is an operation schematic diagram of the thermostatic system according to some embodiments of the present disclosure.

For the device used in the in vitro test of the present disclosure, please refer to FIG. 2. FIG. 2 is an operation schematic diagram of the thermostatic system according to some embodiments of the present disclosure. The operation system has a sonoporation gene transfection device 210, an US animal-imaging device 220, a water bath 230, a 37° C. plastic tube 240, an agarose phantom 250 and a perfusion zone 260. Among them, the 37° C. plastic pipe 240, the agarose phantom 250 and the perfusion zone 260 are used to simulate the temperature environment (37° C. to 38° C.) in guinea pig ears.

For the microbubbles, the temperature-sensitive hydrogel, the temperature-sensitive drug hydrogel, the temperature-sensitive microbubbles drug hydrogel or the combination thereof in the aforementioned preparation, please refer to the following embodiments to understand the properties and the detection data thereof.

Example 1

The Properties of the Microbubbles of the Temperature-Sensitive Microbubbles Drug Hydrogel Example 1 mainly illustrates whether the combination of the microbubbles and the temperature-sensitive hydrogel would affect the stability and existence thereof.

(1) The Particle Diameter and the Zeta Potential Analysis of the Temperature-Sensitive Microbubbles Hydrogel This part is to use Dynamic Light Scattering (DLS) to analyze the particle diameter of the temperature-sensitive microbubbles hydrogel, and measure the zeta potential. By measuring the particle diameter distribution at different time points, we can show the tendency of particles. The intensity of scattered light will also change with time, so as to calculate the particle diameter of the microbubbles and examine the stability.

As shown in FIG. 3A, FIG. 3A is a particle diameter curve diagram of the microbubbles and the microbubbles after mixing with the temperature-sensitive hydrogel according to some embodiments of the present disclosure. It can be seen from the figure that, the average particle diameter of the microbubbles with albumin shell is about 1.7±0.22 μm, while the average particle diameter of the microbubbles in the temperature-sensitive microbubble gel is about 2.8±0.38 μm. At this point, the concentration of the microbubbles in the temperature-sensitive hydrogel is 4.2±0.223×10$^9$ per mL of the temperature-sensitive hydrogel. FIG. 3A shows that, when the microbubbles are included in the temperature-sensitive hydrogel, the particle diameter of the microbubbles will increase.

Then refer to FIG. 3B, FIG. 3B is a zeta potential analysis diagram of the microbubbles and the microbubbles after mixing with the temperature-sensitive hydrogel according to some embodiments of the present disclosure. As shown in FIG. 3B, the average potential of ultra-pure water (Milli-Q, hereinafter referred to as MQ) is 0 mV. The average potential of MQ mixed with the microbubbles is about −2.52±0.79 mV. The average potential of MQ mixed with P407 is about −0.133±0.041 mV. The average potential of MQ mixed with microbubble and P407 is about −2.35±0.798 mV. The average potential of saline is about −0.463±1.366 mV. The average potential of saline mixed with the microbubbles is about −0.70±0.07 mV. The average potential of saline mixed with P407 is about −1.969±0.465 mV. The average potential of saline solution, the microbubbles mixed with P407 is about −1.18±0.40 mV. According to FIG. 3B and the above, the potential of the temperature-sensitive microbubbles hydrogel would present a slightly negative state whether it is mixed with MQ or saline. However, the comparison between MQ and saline showed that saline has better surface tension, which could increase the permeability and delivery efficiency of the drug. Therefore, saline is selected as the basis for subsequent experiments from the similar results.

(2) Optical Qualitative Analysis of the Temperature-Sensitive Microbubbles Hydrogel In this part, saline and the microbubbles are mixed with P407, and placed at 4° C. to observe the survival rate of the microbubbles under an upright microscope. The experimental groups are, respectively, the microbubbles and saline; saline, the microbubbles and 12.5% P407; saline, the microbubbles and 14.5% P407. The observation times are 0 minute, 5 minutes and 1 hour respectively.

Figure 4:
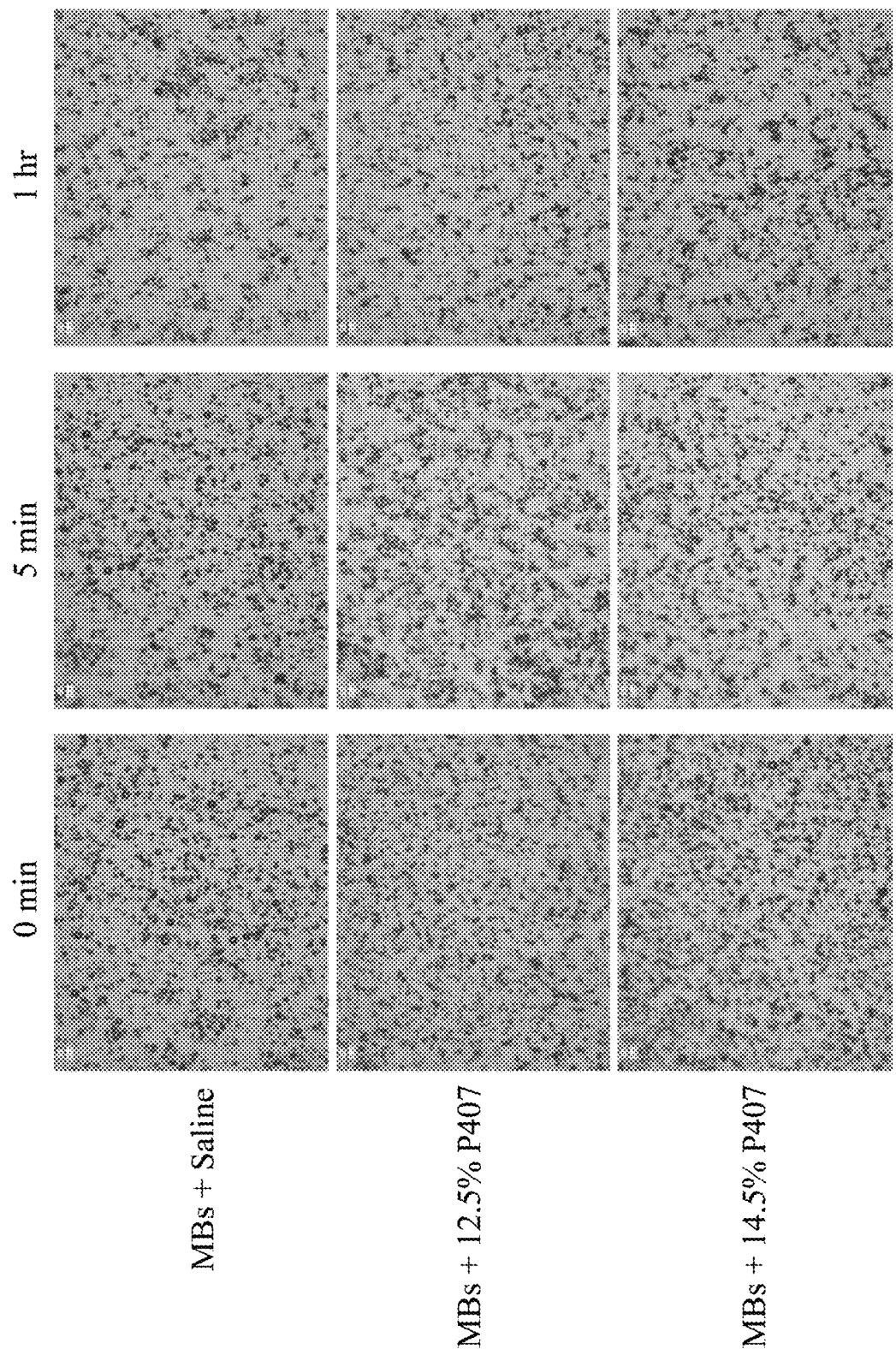
FIG. 4 is a microscopic image of optical qualitative analysis of the microbubbles and the microbubbles after mixing with temperature-sensitive hydrogel at different concentration according to some embodiments of the present disclosure.

As shown in FIG. 4, FIG. 4 is a microscopic image of optical qualitative analysis of the microbubbles and the microbubbles after mixing with temperature-sensitive hydrogel at different concentration according to some embodiments of the present disclosure. The microbubbles diameter of the group of saline mixed with microbubbles and 14.5% P407 is larger than that of the other groups, but there is no significant difference in the microscopic images of the other two groups. It can be concluded that mixing the microbubbles with the temperature-sensitive hydrogels of different concentrations does not affect the survival rate of the microbubbles.

Example 2

Efficiency Analysis of the Temperature-Sensitive Microbubble Hydrogels Treated by Ultrasonic Wave Example 2 mainly describes the destruction efficiency of the microbubbles after the temperature-sensitive microbubbles hydrogel is treated with ultrasonic wave and the microbubbles are destroyed by ultrasonic wave. This experiment uses the thermostatic system of FIG. 2, a probe center frequency of the US animal-imaging device 220 is 40 MHz (its converter is 12 mm, 7 mm in diameter and focus fixed on the resolution of 30 microns). The microbubbles are kinds of contrast agent, and could enhance brightness of ultrasound images. Thus, the brightness would decrease after the microbubbles are destroyed. Accordingly, the inertial cavitation effect is observed by the ultrasonic imaging system.

(1) After the temperature-sensitive microbubbles hydrogel is injected into the perfusion zone 260, the image of the initial temperature-sensitive microbubbles hydrogel is taken by the US animal-imaging device 220. Then, the microbubbles in the temperature-sensitive microbubbles hydrogel in the perfusion zone 260 is destroyed by the sonoporation gene transfection device 210 with a central frequency of 1 MHz and an average power of 3 W/cm$^2$. Finally, the destruction efficiency is converted by the following formula.

Destruction efficiency={[Brightness after treating with ultrasonic wave ($L_n$)−Brightness before treating with ultrasonic wave ($L_0$)]/Brightness before treating with ultrasonic wave ($L_0$)}×100%

(2) In this example, the temperature-sensitive microbubbles hydrogel contains saline, the microbubbles and P407, in which the concentrations of P407 are divided into 0% group (that is, only saline and the microbubbles), 2% group, 8% group, 10% group, 12.5% group, 14.5% group and 17% group.

Figure 5:
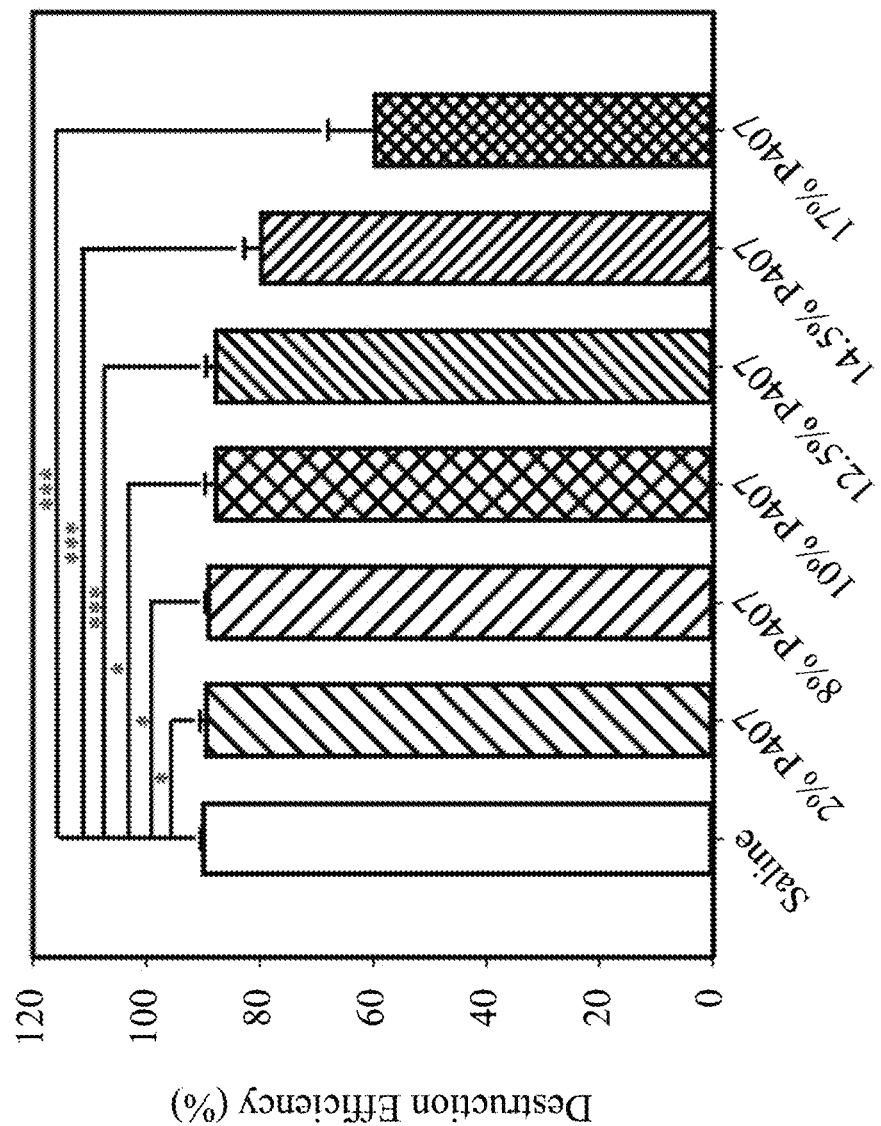
FIG. 5 is a destruction efficiency diagram of the microbubbles and the microbubbles after mixing with temperature-sensitive hydrogel at different concentration, and after destroyed by ultrasonic wave to complete cavitation effect to release energy, according to some embodiments of the present disclosure.

Please refer to FIG. 5, FIG. 5 is a destruction efficiency diagram of the microbubbles and the microbubbles after mixing with temperature-sensitive hydrogel at different concentration, and after destroyed by ultrasonic wave to complete cavitation effect to release energy, according to some embodiments of the present disclosure. FIG. 5 shows that the average destruction efficiency of 0% P407 group is 89.97%, 2% P407 group is 89.42%, 8% P407 group is 89.09%, 10% P407 group is 87.70%, 12.5% P407 group is 87.77%, 14.5% P407 group is 79.75%, and 17% P407 group is 59.77%. According to the above description, in some embodiments, the higher the concentration of P407 in the temperature-sensitive microbubbles hydrogel, the lower the efficiency of the microbubble being destroyed by ultrasonic wave. Such characteristics may be due to the high concentration of P407 would lead to the increase of viscosity of the temperature-sensitive microbubbles hydrogel. Thus, the microbubbles couldn't be fully destroyed, and may also affect the cavitation effect. Then, significant statistical differences are found from 12.5% group to 0% P407 group (P<0.001), so 14.5% group and 17% P407 group should not be preferred. Furthermore, only when the temperature-sensitive properties of P407 are induced can the effect of the in-situ treatment of the present disclosure be achieved. Thus, the 12.5% P407 group may be a better concentration choice. However, it should be noted that, the concentrations described here are only exemplary, and other concentration groups capable of achieving cavitation effect and destroying the microbubbles are also included in the scope of the present disclosure.

Example 3

Analysis of Viscosity of the Temperature-Sensitive Hydrogels, the Temperature-Sensitive Microbubbles Hydrogel and the Temperature-Sensitive Microbubbles Drug Hydrogels Example 3 mainly describes that, for drug delivery compositions, variations in viscosity with respect to temperature are analyzed at different mixing stages. Moreover, according to the results of viscosity analysis, the main formulations and mixing concentrations would be used in the following examples. In this example, a rotational rheometer is used to measure the viscosity. A sample of 100 μL is drawn to the loading table for each measurement at 8° C.-40° C., 0° of a rotor Angle, and 1/50 of a shear rate.

Figure 6A:
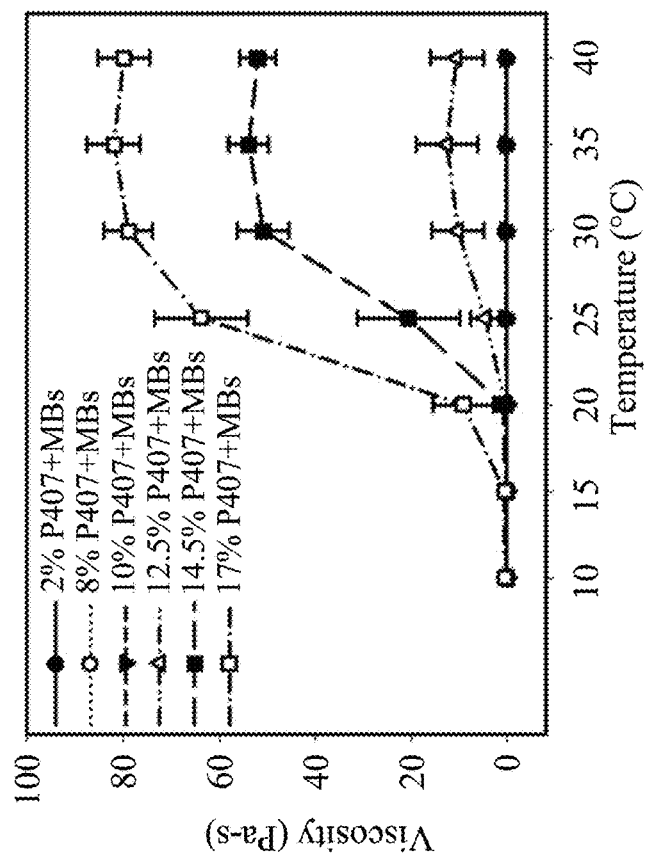
FIG. 6A is a viscosity curve diagram of the temperature-sensitive hydrogel at different concentration according to some embodiments of the present disclosure.

(1) Refer to FIG. 6A for the viscosity curves of the temperature-sensitive hydrogel P407 of the present disclosure without any addition of other materials. FIG. 6A is a viscosity curve diagram of the temperature-sensitive hydrogel at different concentration according to some embodiments of the present disclosure. As can be seen from the figure, when the concentrations of P407 are 2%, 8% and 10%, the gel-forming situation is not obvious. When the concentrations of P407 are 12.5%, 14.5% and 17%, the gel-forming is obvious. When the concentrations of P407 are 12.5%, 14.5% and 17%, the gel-forming temperatures are about 33.5° C., about 24.2° C., and about 24.0° C., respectively. The higher the concentration of P407, the lower the gel-forming temperature. The viscosities of the above temperature-sensitive hydrogels are shown in Table 1 below.

TABLE 1

Viscosities of the temperature-sensitive hydrogels at different temperatures and concentrations (unit: Pa · S)

| Temperature(° C.) | Group | | | | | |
|---|---|---|---|---|---|---|
| | 2% P407 Viscosity | 8% P407 Viscosity | 10% P407 Viscosity | 12.5% P407 Viscosity | 14.5% P407 Viscosity | 17% P407 Viscosity |
| 10 | $3.13 \times 10^{-3}$ | $6.51 \times 10^{-3}$ | 0.0127 | 0.0177 | 0.0254 | 0.0385 |
| 15 | $2.82 \times 10^{-3}$ | $5.65 \times 10^{-3}$ | 0.0114 | 0.0161 | 0.0282 | 0.062 |
| 20 | $2.38 \times 10^{-3}$ | $4.93 \times 10^{-3}$ | 0.0126 | 0.0226 | 0.0881 | 1.2202 |
| 25 | $2.06 \times 10^{-3}$ | $5.05 \times 10^{-3}$ | 0.0205 | 0.0675 | 3.13 | 6.3802 |
| 30 | $1.83 \times 10^{-3}$ | $5.11 \times 10^{-3}$ | 0.0243 | 0.4177 | 5.5921 | 7.8825 |
| 35 | $1.67 \times 10^{-3}$ | $4.56 \times 10^{-3}$ | 0.0238 | 0.9336 | 5.7578 | 8.0391 |
| 40 | $1.51 \times 10^{-3}$ | $3.94 \times 10^{-3}$ | 0.0264 | 0.9226 | 5.5423 | 7.8033 |

Figure 6B:
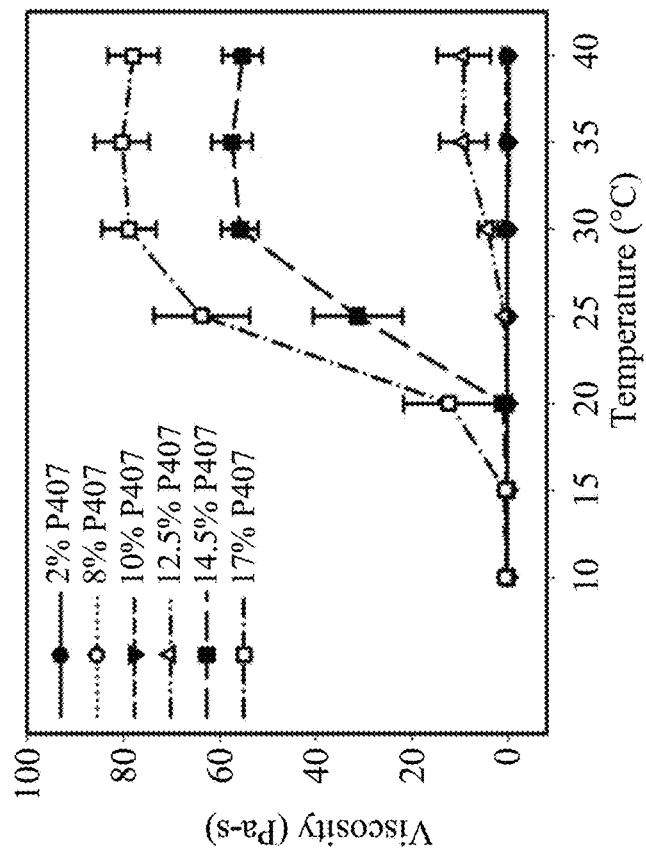
FIG. 6B is a viscosity curve diagram of the microbubbles mixing with the temperature-sensitive hydrogel at different concentration according to some embodiments of the present disclosure.

In the present disclosure, for the viscosity curves of the temperature-sensitive microbubble hydrogels without the addition of drugs (temperature-sensitive hydrogel P407+ microbubbles), please refer to FIG. 6B. FIG. 6B is a viscosity curve diagram of the microbubbles mixing with the temperature-sensitive hydrogel at different concentration according to some embodiments of the present disclosure. As can be seen from the figure, when P407 at different concentrations are added with microbubbles, the viscosities of P407 at different concentrations do not change significantly, compared with those of P407 alone (FIG. 6A). When the concentration of P407 is 12.5%, the gel-forming temperature drops to about 26.9° C. after adding microbubbles. Therefore, it can be seen that when P407 and microbubbles are mixed, the gel-forming temperature may drop. In FIG. 6A and FIG. 6B, it can be seen that when the concentrations of P407 are 14.5% and 17%, the gel-forming temperatures are lower than those of other groups, and the viscosities increase greatly during gel-forming. If combined with drugs for cavitation effect and in-situ treatment, it will be relatively difficult to operate because of the viscosities. Therefore, groups with 10% and 12.5% concentrations of P407 would be selected for subsequent examples. The viscosities of the temperature sensitive microbubble hydrogels above are shown in Table 2 below.

TABLE 2

Viscosities of the temperature-sensitive microbubbles hydrogels at different temperatures and concentrations (unit: Pa · S)

| Groups Temperature(° C.) | 2% P407 Viscosity | 8% P407 Viscosity | 10% P407 Viscosity | 12.5% P407 Viscosity | 14.5% P407 Viscosity | 17% P407 Viscosity |
| --- | --- | --- | --- | --- | --- | --- |
| 10 | $2.47 \times 10^{-3}$ | 0.0101 | 0.0124 | 0.0179 | 0.0257 | 0.0432 |
| 15 | $2.20 \times 10^{-3}$ | $8.73 \times 10^{-3}$ | 0.0113 | 0.0182 | 0.0285 | 0.0549 |
| 20 | $1.92 \times 10^{-3}$ | $8.66 \times 10^{-3}$ | 0.0147 | 0.0368 | 0.0861 | 0.9118 |
| 25 | $1.62 \times 10^{-3}$ | 0.0125 | 0.0258 | 0.459 | 2.0632 | 6.3829 |
| 30 | $1.40 \times 10^{-3}$ | 0.0142 | 0.0316 | 1.0179 | 5.1005 | 7.898 |
| 35 | $1.22 \times 10^{-3}$ | 0.0128 | 0.0426 | 1.2558 | 5.3975 | 8.2001 |
| 40 | $1.07 \times 10^{-3}$ | 0.0117 | 0.0449 | 1.0487 | 5.2112 | 7.9927 |

Figure 6C:
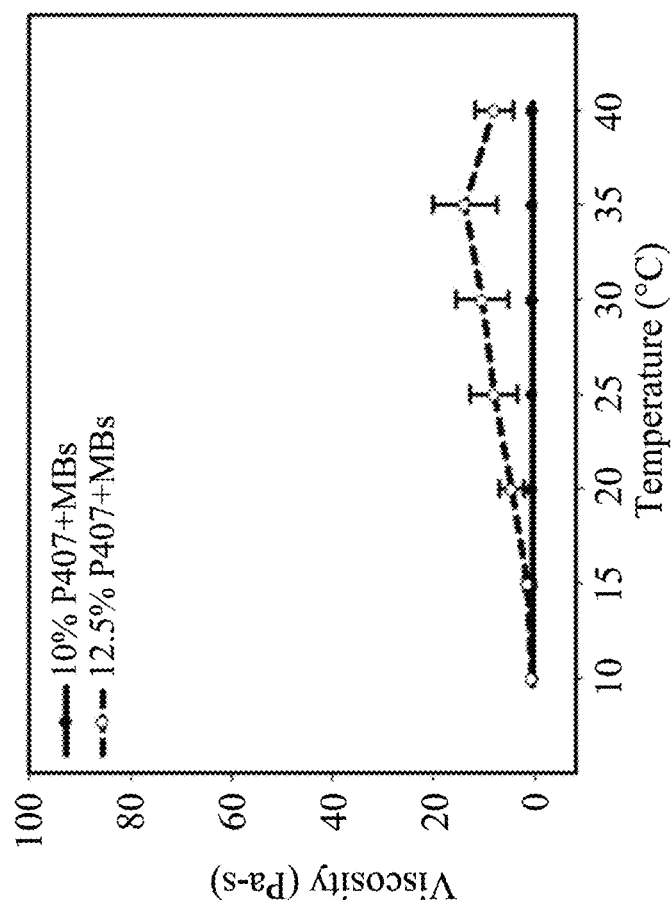
FIG. 6C is a viscosity curve diagram of the microbubbles mixing with the temperature-sensitive hydrogel at different concentration and DEX according to some embodiments of the present disclosure.

For the viscosity curves of the temperature-sensitive microbubbles drug hydrogels of different temperatures of the present disclosure, please refer to FIG. 6C. FIG. 6C is a viscosity curve diagram of the microbubbles mixing with the temperature-sensitive hydrogel at different concentration and DEX according to some embodiments of the present disclosure. It can be seen from the figure that, the gel-forming temperature of 12.5% P407 is about 27.0° C. See Table 3 for the viscosity of the temperature-sensitive microbubbles drug hydrogels mentioned above.

TABLE 3

Viscosities of the temperature-sensitive microbubbles drug hydrogels at different temperatures and concentrations (unit: Pa · S)

| | Group | |
| --- | --- | --- |
| Temperature(° C.) | 10% P407 + MBs + DEX Viscosity | 12.5% P407 + MBs + DEX Viscosity |
| 10 | 0.0389 | 0.0596 |
| 15 | 0.0443 | 0.1478 |
| 20 | 0.0553 | 0.4578 |
| 25 | 0.0548 | 0.8029 |
| 30 | 0.0522 | 1.0378 |
| 35 | 0.0491 | 1.3846 |
| 40 | 0.0501 | 0.8076 |

The gel-forming temperatures in FIG. 6A, FIG. 6B and FIG. 6C are the points with the highest slopes on the curves, which means the temperatures at which the viscosity change produces a jump in the process of temperature rise (for example, when the temperature rises from 25° C. to 30° C., the viscosity of 12.5% P407+MBs+DEX group rises from 0.8029 Pa·S to 1.0378 Pa·S. At this point, the slope is (1.0378-0.8029)/(30-25)=0.04698). It should be noted that although subsequent examples would focus on P407 concentrations of 10% and 12.5%, the above 2%, 8%, 14.5% and 17% are still the concentrations that can achieve the efficacy of the present disclosure. Therefore, the foregoing concentrations are also included in the scope of the present disclosure.

Example 4

In Vitro Diffusion Experiment of the Temperature-Sensitive Microbubbles Drug Hydrogels Example 4 mainly describes the diffusion effect of the temperature-sensitive microbubbles drug hydrogels. The experiment mixes the temperature-sensitive microbubbles drug hydrogels with fluorescein isothiocyanate (hereinafter referred to as the FITC), which forms the degradation temperature-sensitive microbubbles drug hydrogels. The degradation temperature-sensitive microbubbles drug hydrogels are combined with Franz diffusion cell to be as drug delivery models. At the same time, the drug delivery models are divided into ultrasonic group (or referred to as US) and the unapplied group (which is without ultrasonic treatment). According to the time before and after the treatment of ultrasonic wave, samples from the diffusion end of the diffusion cell in each group are extracted. Finally, the absorbance of the samples in each group is detected.

Figure 7A:
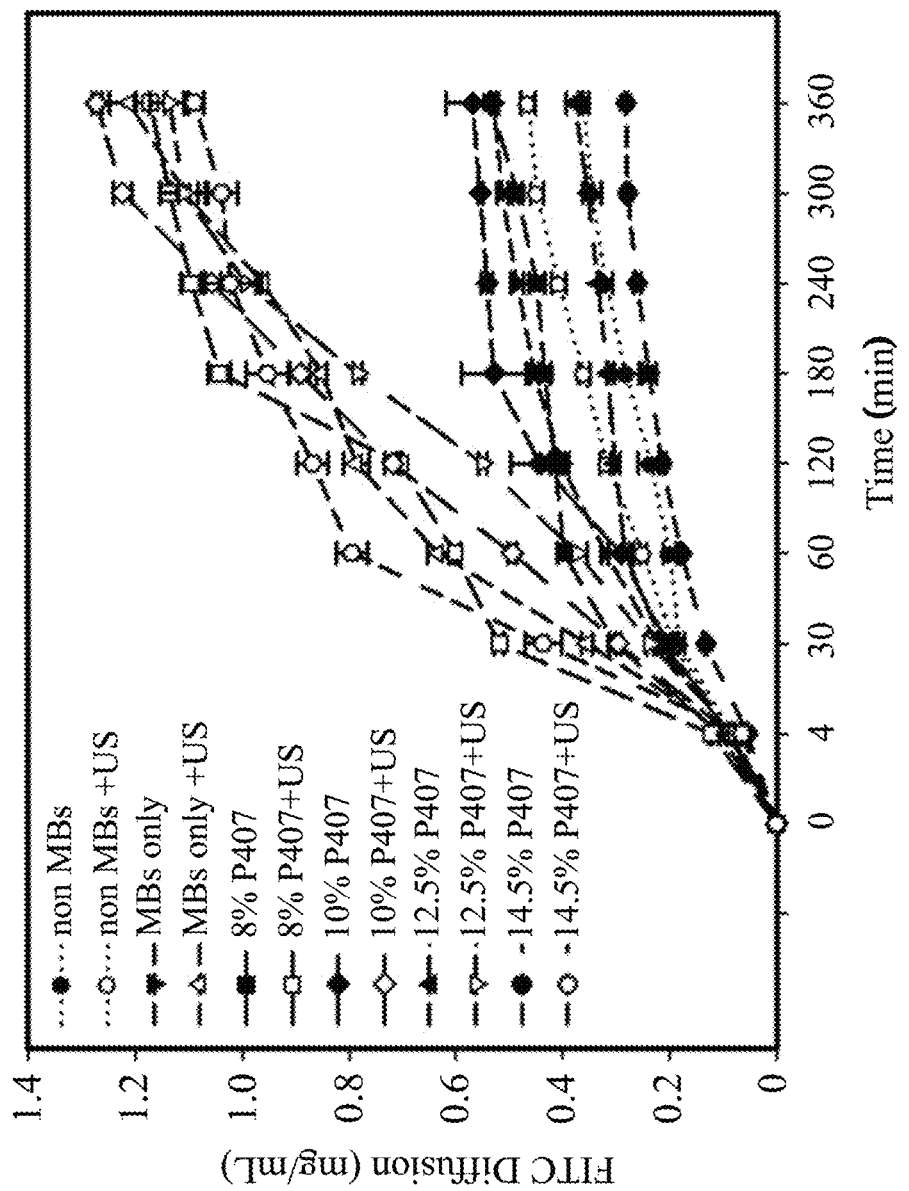
FIG. 7A is a line graph of in vitro fluorescein isothiocyanate (FITC) diffusion assay of the drug delivery composition according to some embodiments of the present disclosure.

(1) For the diffusion effects of the temperature-sensitive microbubbles drug hydrogels at different concentrations, please refer to FIG. 7A. FIG. 7A is a line graph of in vitro fluorescein isothiocyanate (FITC) diffusion assay of the drug delivery composition according to some embodiments of the present disclosure. It can be seen from the figure that, the diffusion effects of the groups with ultrasonic treatment is obviously better than those of the groups without ultrasonic treatment. Moreover, in the groups with ultrasonic treatment, the diffusion effects of the groups with microbubbles are better than those of the groups without microbubbles. Moreover, the higher the concentration of P407, the lower the diffusion effect. It also indicates that the increase of viscosity would affect the efficiency of ultrasonic wave to destroy microbubbles and the diffusion effect caused by cavitation effect.

Figure 7B:
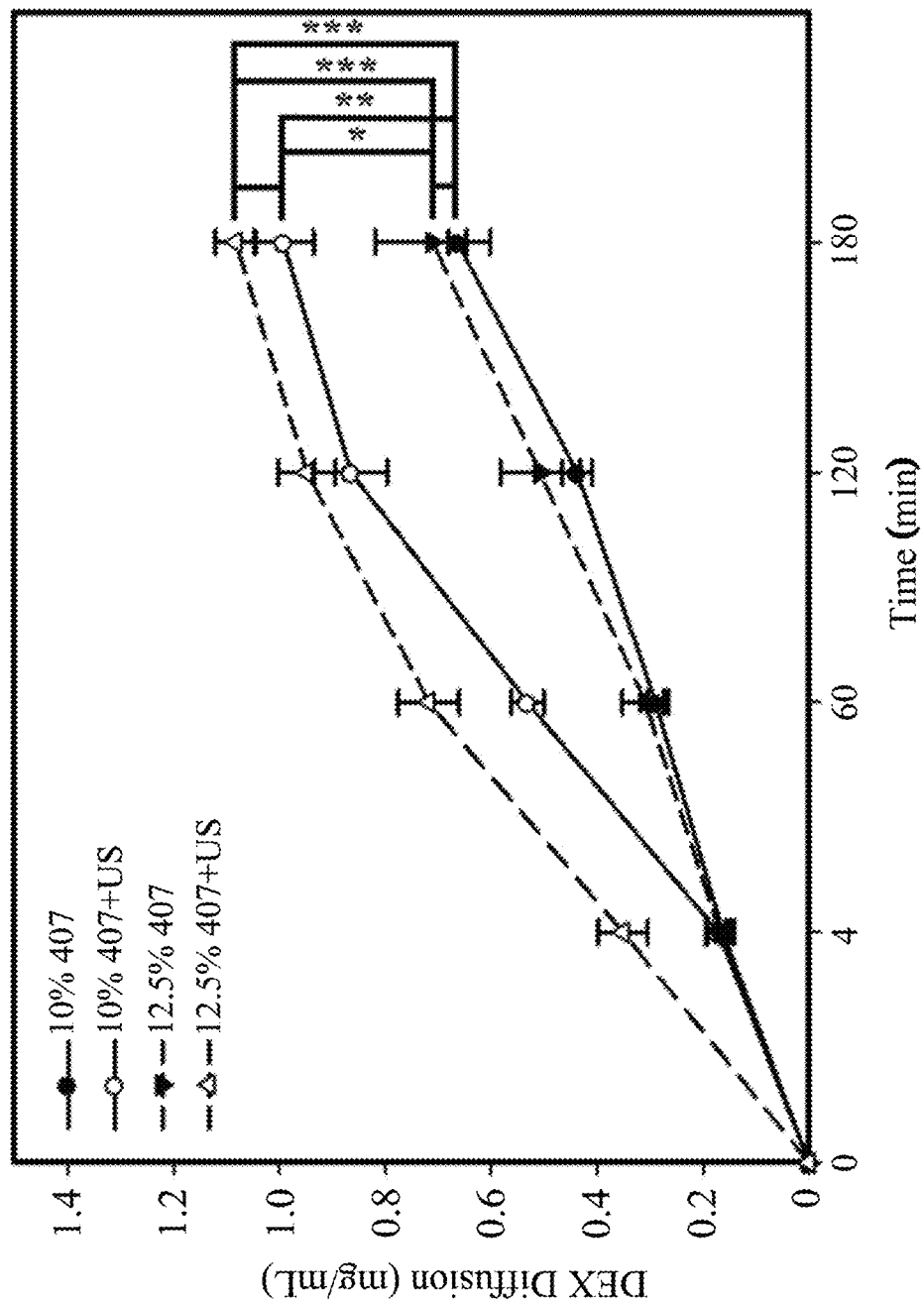
FIG. 7B is a line graph of in vitro DEX diffusion assay of the drug delivery composition according to some embodiments of the present disclosure.

(2) Similar to the results of the previous example, the present example further analyzes the groups with and without ultrasonic treatment of 10% P407 and 12.5% P407. Please refer to FIG. 7B, FIG. 7B is a line graph of in vitro DEX diffusion assay of the drug delivery composition according to some embodiments of the present disclosure. In the group without ultrasonic treatment, the average dose of DEX in 10% P407 is about 0.662±0.017 mg/mL, and the average dose of DEX in 12.5% P407 is about 0.771±0.109 mg/mL. In the group treated with ultrasonic wave, the average dose of DEX in 10% P407 is about 0.993±0.056 mg/mL, and the average dose of DEX in 12.5% P407 is about 1.083±0.037 mg/mL. As can be seen from the figure and the above data, the concentration of DEX in the group of the 12.5% P407 with ultrasonic treatment is the highest at any time point. Moreover, the concentration of DEX released in group of the 10% P407 with ultrasonic treatment is higher than that without ultrasonic treatment.

According to FIG. 7A and FIG. 7B, although P407 combined with microbubbles and ultrasonic treatment at various concentrations could have good drug release and diffusion effects, the drug diffusion effect of 12.5% P407 is much more obvious. Thus, the following animal experiments would be mainly carried out with 12.5% P407. It should be noted that the 12.5% P407 group is only a preferable example, and should not be used to limit the present disclosure. Other effective concentration groups are also covered by the scope of the present disclosure.

Example 5

Detection of Perilymphatic Fluid of the Inner Ear in Guinea Pig Models

All Animal experiments are approved by the NDMC-TSGH Institutional Animal Care and Use Committee (IA-CUC).

(1) Preparation of guinea pig models: The guinea pig model used in this example is the pigmented guinea pig model. The surgical anesthesia is given by intramuscular injection of ketamine HCl (40 mg per kg guinea pig body weight). The remaining injections are muscle relaxant Rompun® (Xylazine)(10 mg/kg guinea pig body weight), prophylactic antibiotic chloramphenicol sodium succinate (30 mg/kg guinea pig body weight), and local anesthetic Lidocaine HCl (1%, 0.5 mL).

(2) Preparation for the Guinea pig surgery and the experiment: The surgery is carried out by intratympanic injection. The guinea pig is anesthetized and operated under a dissecting surgical microscope after confirmation. A 22G needle is used to puncture the eardrum, and 200 µL of the temperature-sensitive microbubbles drug (DEX) hydrogel of the present disclosure is applied into the middle ear cavity. The experiments are performed in the ultrasound microbubble treatment group (USM), round window soaking group (RWS), and the group treated with DEX only without MBs (DEX only without MBs). The groups are as follows: USM group is injected with the temperature-sensitive microbubbles drug hydrogel at 3W energy for 1 minute. In RWS group, only the temperature-sensitive microbubbles drug hydrogel is injected into the middle ear cavity, which is without the ultrasonic treatment. In DEX only without MBs group, DEX aqueous solution of the same concentration is applied to the middle ear cavity. The concentrations of DEX are measured in the cochlear perilymph of guinea pigs on day 1 and day 7 after injection.

Figures 8A, 8B:
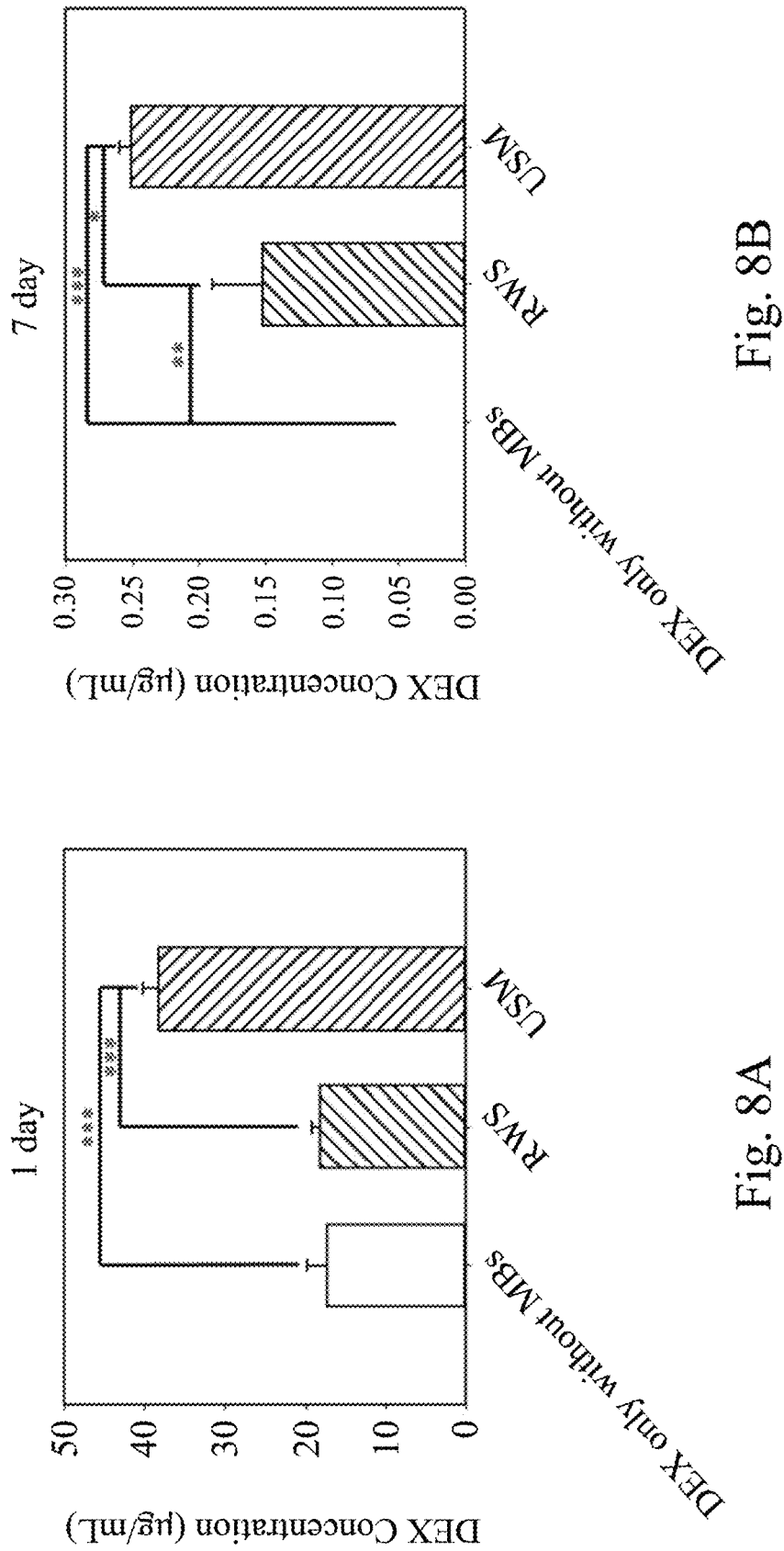
FIG. 8A is a bar chart of DEX concentration in the inner ear after treating guinea pig with the drug delivery composition for 1 day according to some embodiments of the present disclosure.
FIG. 8B is a bar chart of DEX concentration in the inner ear after treating guinea pig with the drug delivery composition for 7 days according to some embodiments of the present disclosure.

The results on day 1 after injection are shown in FIG. 8A. FIG. 8A is a bar chart of DEX concentration in the inner ear after treating guinea pig with the drug delivery composition for 1 day according to some embodiments of the present disclosure. The concentrations measures in USM group, RWS group and DEX only without MBs group are about 38.25±1.96 µg/mL, about 18.29±1.05 µg/mL and about 17.38±2.51 µg/mL, respectively. According to the figure and the above data, the temperature-sensitive microbubbles drug hydrogel of the present disclosure of USM group significantly improved the efficiency of DEX entering the inner ear of guinea pigs, compared with RWS group and DEX only group.

The results on day 7 after injection are shown in FIG. 8B. FIG. 8B is a bar chart of DEX concentration in the ear after treating guinea pig with the drug delivery composition for 7 days according to some embodiments of the present disclosure. The measured concentrations are about 0.25±0.02 µg/mL in USM group, 0.15±0.09 µg/mL in RWS group, and <3 ng/mL in DEX only group. According to the figure and the above data, the temperature-sensitive microbubbles drug hydrogel of the present disclosure on day 7 after ultrasonic treatment could retain more drugs in the inner ear of guinea pigs than those in RWS group and DEX only group. Accordingly, the temperature-sensitive microbubbles drug hydrogel of the present disclosure combined with ultrasonic treatment can not only deliver the drug immediately from the middle ear to the inner ear, but also provide a long-term and stable drug release.

Example 6

Analysis of DEX Uptake in Cochlear Hair Cells of Guinea Pig Models After Sacrifice After sacrificing the guinea pigs of USM group, RWS group and DEX only group in example 5, the cochlear tissues are removed and observed under confocal microscope. In this example, cochlear hair cells are labeled by phalloidin and Myosin 7a. Then, anti-DEX antibody is used to detect the uptake of DEX in the cochlear hair cells.

Figure 9:
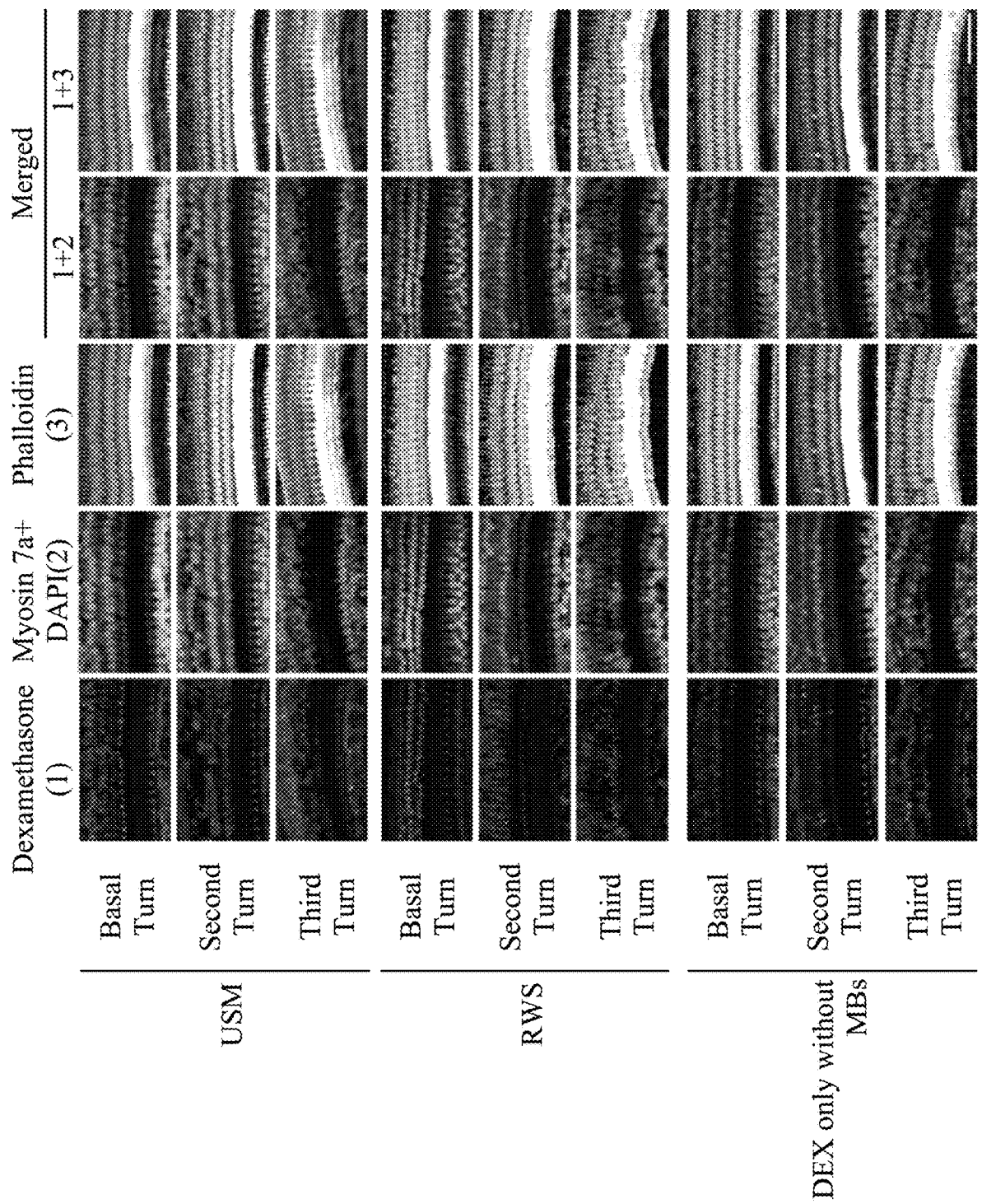
FIG. 9 is a fluoroscopic diagram (using a confocal microscope, 50 μm in scale) of the cochlea of a guinea pig after treating with the drug delivery composition for 1 day according to some embodiments of the present disclosure.

The results on day 1 after injection are shown in FIG. 9. FIG. 9 is a fluoroscopic diagram (using a confocal microscope, 50 µm in scale) of the cochlea of a guinea pig after treating with the drug delivery composition for 1 day according to some embodiments of the present disclosure. As shown in FIG. 9, on day 1 after injection, compared with RWS group and DEX only without MBs group, USM group shows more obvious fluorescence expression of DEX in cochlear hair cells, especially in basal turn. It can be seen that the temperature-sensitive microbubbles drug hydrogel of the present disclosure does release DEX into the inner ear after ultrasonic treatment, thereby enhancing drug uptake by cochlear hair cells.

Figure 10:
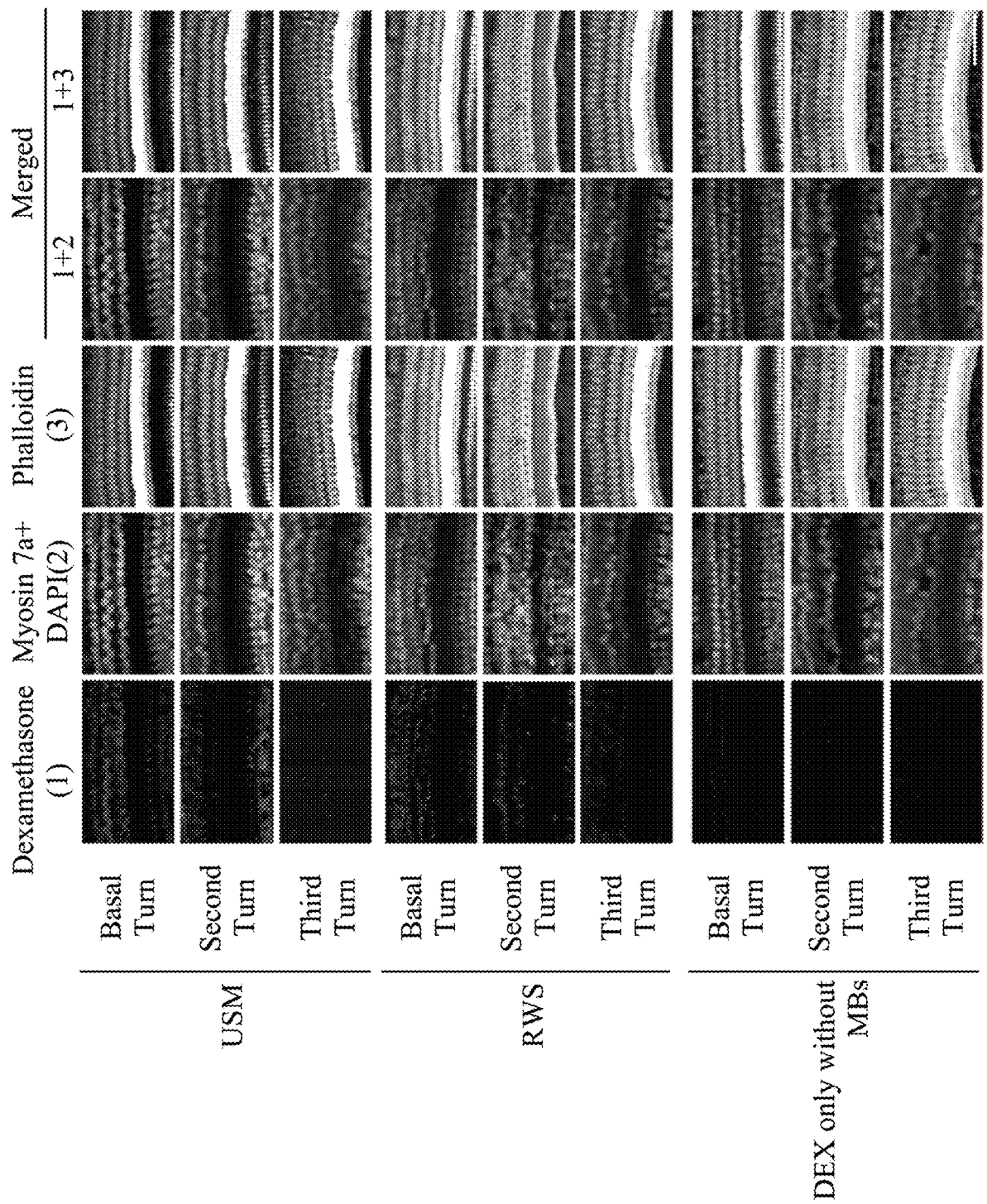
FIG. 10 is a fluoroscopic diagram (using a confocal microscope, 50 μm in scale) of the cochlea of a guinea pig after treating with the drug delivery composition for 7 days according to some embodiments of the present disclosure.

The results on day 7 after injection are shown in FIG. 10. FIG. 10 is a fluoroscopic diagram (using a confocal microscope, 50 µm in scale) of the cochlea of a guinea pig after treating with the drug delivery composition for 7 days according to some embodiments of the present disclosure. As can be seen from FIG. 10, on day 7 after injection, compared with RWS group and DEX only without MBs group, USM group still shows fluorescence of DEX in cochlear hair cells. It could be concluded that the temperature-sensitive microbubbles drug hydrogel of the present disclosure has a long release effect of at least one week after ultrasonic treatment.

Example 7

The Staining of the Middle Ear Cavity Tissue Section of Guinea Pigs on Day 28 After Injection (1) Sampling of tympanic bulla: On day 28 after the injection of temperature-sensitive microbubbles drug hydrogel, the guinea pigs are anesthetized and sacrificed. Then, the tympanic bullas are removed. The tympanic bullas are fixed with 4% formalin for 1 hr at room temperature, followed by soaking and rotating the cochlea at 4° C. in 10% EDTA at pH 7.3 to decalcify. The tympanic membrane and the surrounding parts of the middle ear cavity are separated from the tympanic bullas for histological examination. The samples are dehydrated with graded ethanol solution, cleaned with xylene, and then encapsulated and embedded with paraffin. Finally, the embedded samples are cut into 3 mm tissue sections.

(2) Tissue staining analysis: Hematoxylin and eosin (H&E) staining is performed on tissue sections, followed by observation and recording by optical microscope.

(3) Sample grouping: The samples were divided into USM, RWS, intratympanic saline injection group (ITS) and positive control group. The USM group and the RWS group are the same as the previous examples. The ITS group is injected saline into the tympanic cavity without the microbubbles and drugs. The positive control group is a guinea pig model suffering from otitis media after lipopolysaccharide treatment.

Figure 11:
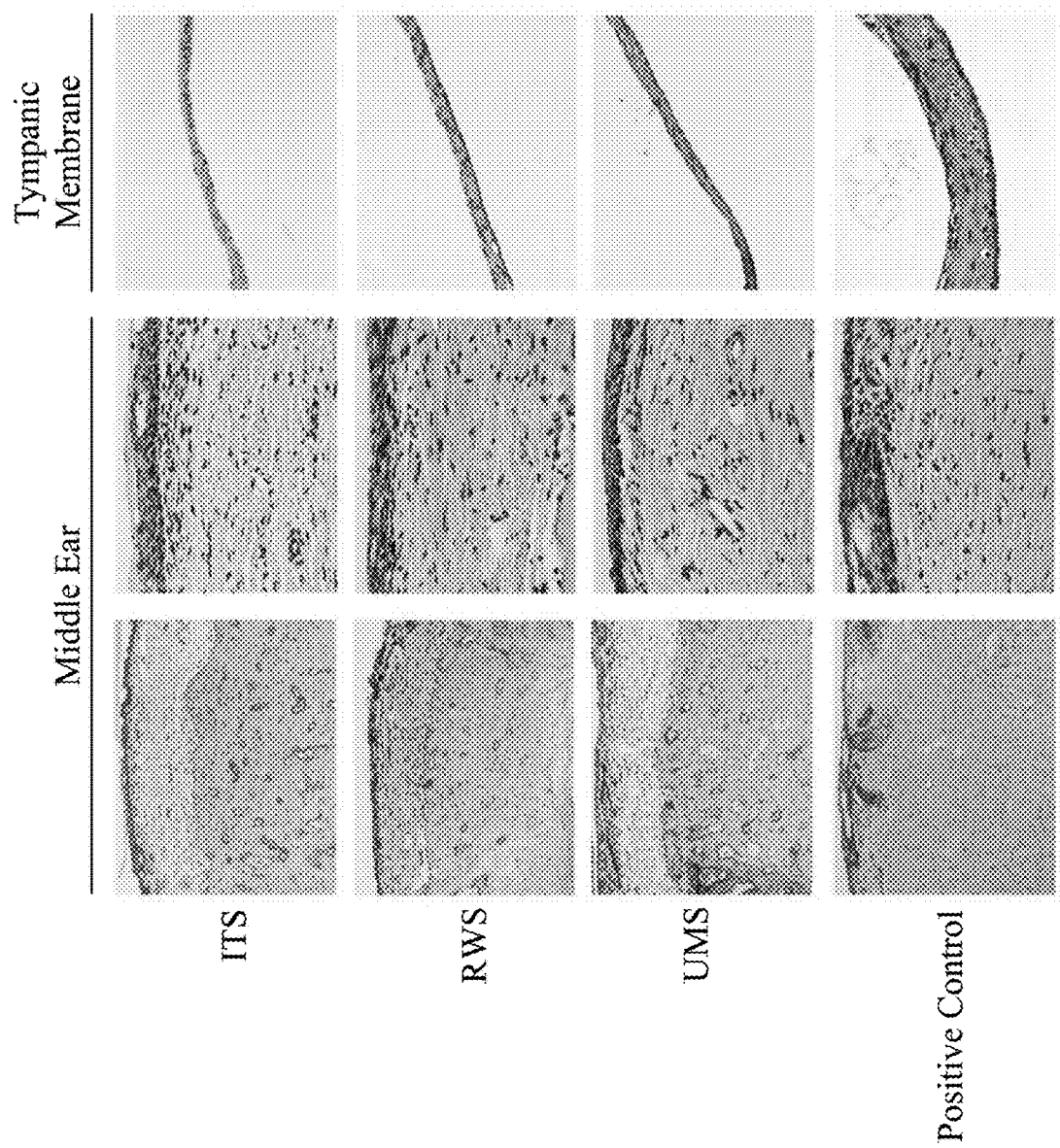
FIG. 11 is a tissue section staining diagram of the middle ear of a guinea pig after treating with the drug delivery composition for 28 days according to some embodiments of the present disclosure (in the first column, the scale is 500 μm, and in the second and third columns, the scale are 50 μm).

The purpose of example 7 is to test whether the temperature-sensitive microbubbles drug hydrogel would induce inflammation of the middle ear on day 28 after injection into the middle ear cavity of guinea pigs. In some embodiments, the results of staining analysis are shown in FIG. 11. FIG. 11 is a tissue section staining diagram of the middle ear of a guinea pig after treating with the drug delivery composition for 28 days according to some embodiments of the present disclosure (in the first column, the scale is 500 µm, and in the second and third columns, the scale are 50 µm). As can be seen from the figure, thickening of the middle ear epithelium and tympanic membrane and many inflammatory cells in the middle ear mucosa were found in the positive control group. The thicknesses of the middle ear mucosa and the tympanic membrane are similar in the USM group, the RWS group and the ITS group, and there are no prominent infiltration of inflammatory cells in these three groups. It could be concluded that the temperature-sensitive microbubbles hydrogel of the present disclosure do not cause inflammation or tissue adverse reactions in the middle ear tissues of guinea pigs on day 28 after the injection and ultrasonic treatment.

Example 8

Damage Analysis of Cochlear Hair Cells in Guinea Pigs (1) Guinea pig tissue sampling: On day 28 after the injection of the temperature-sensitive microbubbles drug hydrogel, the guinea pigs are anesthetized and sacrificed. The removed tympanic bullas are fixed with PBS and formalin, the hard bones are removed by forceps and the organs of Corti are removed, then soaked in 4% Formalin at 4° C. for 24 hours. After fixation, they are cleaned with PBS for 3 times, 10 minutes each time. After antibody staining is added for labeling, they are cleaned with PBS for 3 times, 10 minutes each time. The upper (third turn), middle (second turn) and lower (basal turn) layers of the cochlea are divided by a surgical tool and fixed on the glass slides with DAPI Fluoromount-G. The cover glass slides are sealed with water-based mounting glue and stored at room temperature in the dark.

(2) Sample grouping: The samples are divided into USM, RWS and ITS groups.

Figure 12:
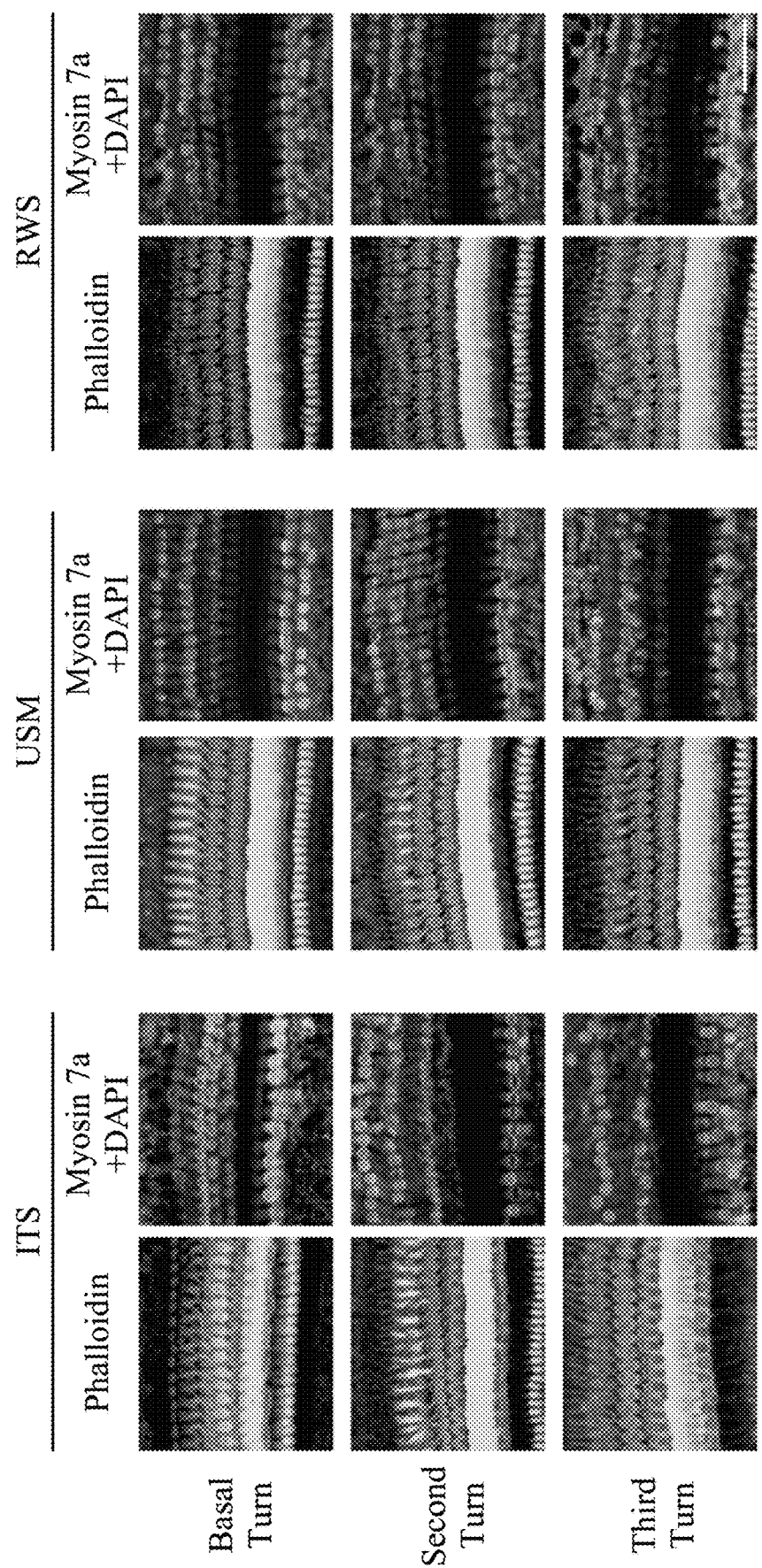
FIG. 12 is a fluoroscopic diagram (using a confocal microscope, 50 μm in scale) of the cochlea of a guinea pig after treating with the drug delivery composition for 28 days according to some embodiments of the present disclosure.

The purpose of this example is to test whether the temperature-sensitive microbubbles drug hydrogel would cause damage to inner ear hair cells. Phalloidin would bind to actin in the scaffold. Myosin 7a is used to label hair cells and can be used to analyze the damage of cochlear tissue under confocal microscopy. For the results of hair cells analysis, please refer to FIG. 12. FIG. 12 is a fluoroscopic diagram (using a confocal microscope, 50 µm in scale) of the cochlea of a guinea pig after treating with the drug delivery composition for 28 days according to some embodiments of the present disclosure. As can be seen from the figure, hair cells in the three layers of each group are neatly arranged, and there are no loss of hair cells. It could be concluded that the temperature-sensitive microbubbles drug hydrogel of the present disclosure does not cause adverse effects on cochlear hair cells after ultrasonic treatment.

Example 9

Hearing Assessment of Inner Ear After Injection in Guinea Pig Models

The purpose of this example is to test whether the auditory response of guinea pigs would be affected by the retention of the temperature-sensitive microbubbles drug hydrogel in the middle ear cavity after the injection of the temperature-sensitive microbubbles drug hydrogel. Auditory brainstem evoked response (ABR) and distortion-product optoacoustic emissions (DPOAE) are performed to operate this example.

(1) Auditory brainstem response: After the guinea pigs are anesthetized and the ear canals are cleaned. Needle electrodes are inserted into the skin of the ear as the positive electrode, into the skin of the top of the head as the negative electrode, and into the skin of the back for as the ground electrode. The specific tone bursts are generated by the monitoring instrument, and the response values of 8 kHz, 12 kHz, 16 kHz, 20 kHz, 24 kHz, 28 kHz, and 32 kHz are detected respectively. Among them, all the experimental groups are the same as the previous examples, namely, the USM group, the RWS group and the ITS group.

(2) Distortion-product optoacoustic emissions: After the guinea pigs are anesthetized and the ear canals are cleaned, the response values are measured at different center frequencies (FC). Two simultaneous continuous pure tones, F1 and F2 are calculated using the FC to yield a frequency of two primary tones (Tone 1 and 2). Two separate speakers (EC1 close-field speakers) are inserted into the guinea pigs' ear canals to generate the two primary tones for eliciting DPOAEs. The two primary tones are presented at the same intensity (65 dB) and at a frequency ratio (F2/F1) of 1.2. The DPOAE recordings are measured with a low-noise microphone and averaged 512 times at each frequency. The peak of the cubic difference distortion product (2F1−F2) at different FCs is accepted as a DPOAE if it is 3 dB above the noise floor, and the difference is referred to as the signal-to-noise ratio (SNR).

Figure 13A:
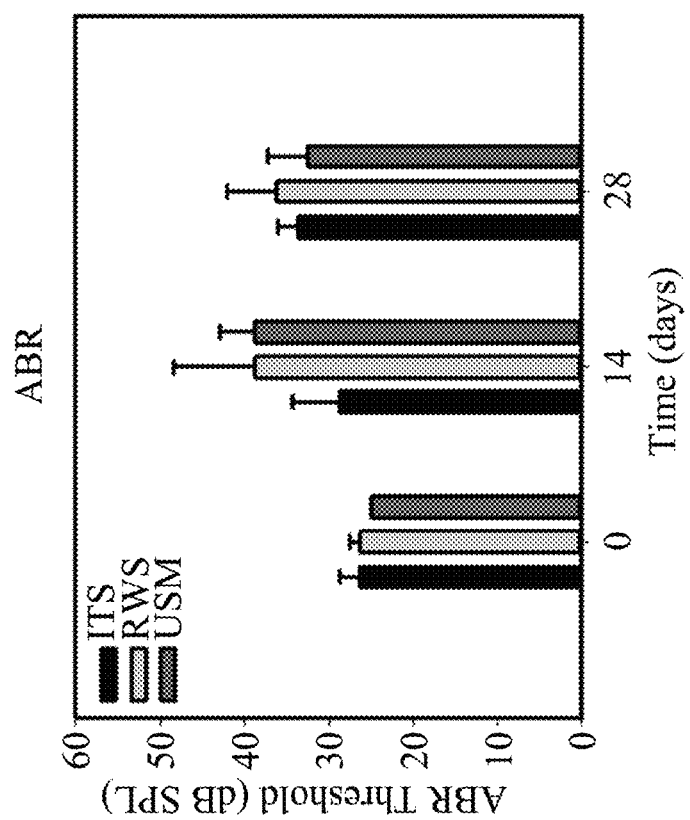
FIG. 13A is a bar chart of click sound response thresholds for auditory brainstem response (ABR) of the ear of a guinea pig after treating with the drug delivery composition for 0 day, 14 days and 28 days according to some embodiments of the present disclosure.
Figure 13B:
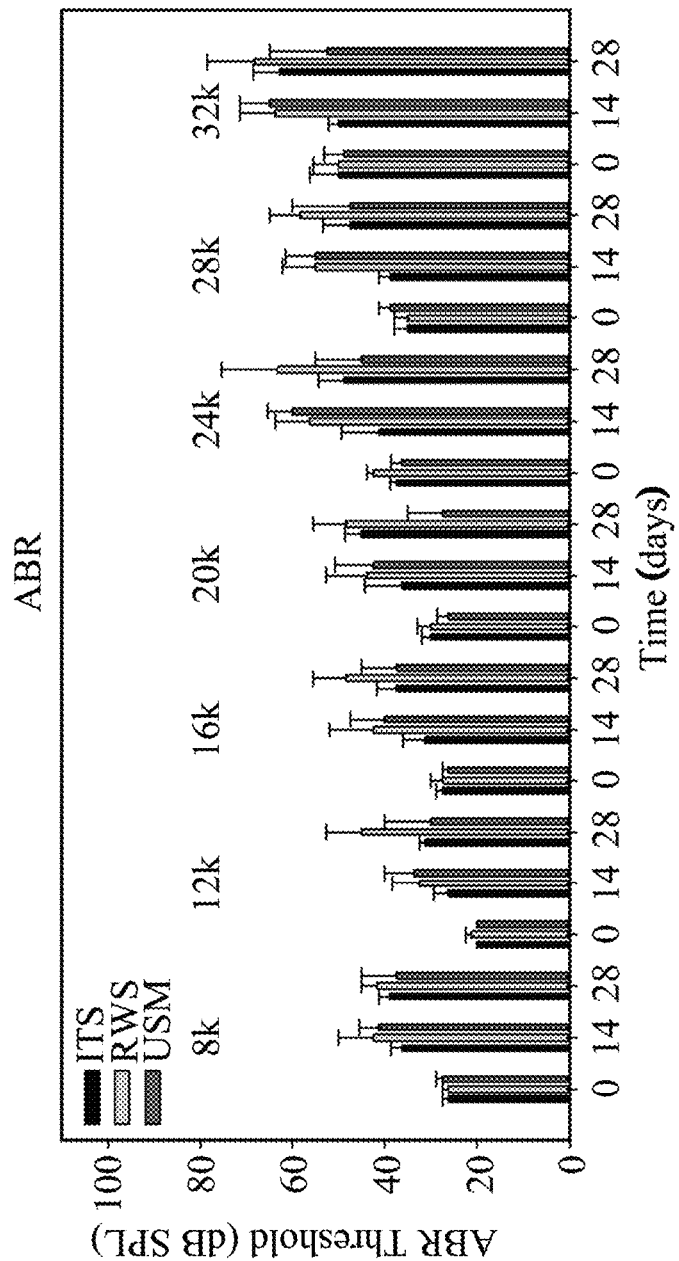
FIG. 13B is a bar chart of variable tone burst sound response thresholds for ABR of the ear of a guinea pig after treating with the drug delivery composition for 0 day, 14 days and 28 days according to some embodiments of the present disclosure.

In some embodiments, the results of auditory brainstem response are shown in FIG. 13A and FIG. 13B. FIG. 13A is a bar chart of click sound response thresholds for auditory brainstem response (ABR) of the ear of a guinea pig after treating with the drug delivery composition for 0 day, 14 days and 28 days according to some embodiments of the present disclosure. FIG. 13B is a bar chart of variable tone burst sound response thresholds for ABR of the ear of a guinea pig after treating with the drug delivery composition for 0 day, 14 days and 28 days according to some embodiments of the present disclosure. As can be seen from the figure, there are no significant differences at each time point between the USM group, the RWS group and the ITS group on day 0, 14 and 28. Therefore, when the temperature-sensitive microbubbles drug hydrogel is injected into the middle ears of guinea pigs followed by the ultrasonic treatment, there is no significant effect on hearing.

Figure 13C:
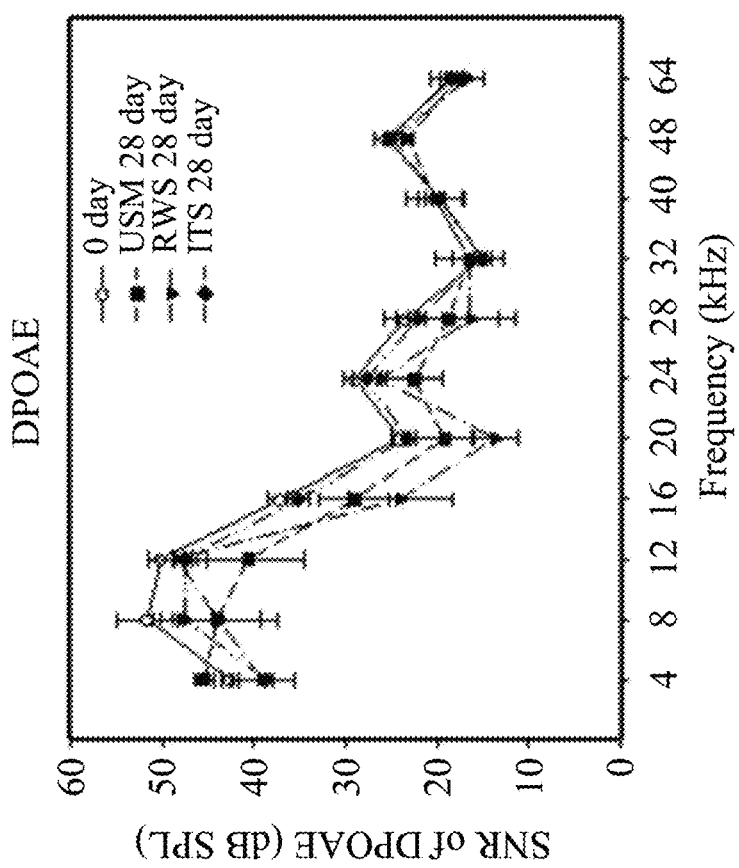
FIG. 13C is a detection line graph of distortion-product otoacoustic emissions (DPOAE) of the ear of a guinea pig after treating with the drug delivery composition for 0 day and 28 days according to some embodiments of the present disclosure. Signal-to-noise ratios (SNRs) of the cubic difference distortion product (2F1–F2) at different center frequencies (FCs) for each group.

In some embodiments, the results of distortion-product optoacoustic emissions, please refer to FIG. 13C. FIG. 13C is a detection line graph of distortion-product optoacoustic emissions (DPOAE) of the ear of a guinea pig after treating with the drug delivery composition for 0 day and 28 days according to some embodiments of the present disclosure. It can be seen from the figure that the SNR of DPOAE in the USM group, the RWS group and the ITS group show no significant differences from 4 kHz to 64 kHz. Therefore, when the temperature-sensitive microbubbles drug hydrogel is injected into the middle ear of guinea pigs followed by the ultrasonic treatment, there is no significant effect on hearing.

In summary, the drug delivery composition of the present disclosure (i.e., the temperature-sensitive microbubbles drug hydrogel) differs from general pharmaceutical gels, which are limited to the surface of the skin and have limited absorption and therapeutic effects. The drug delivery composition of the present disclosure achieves stable long-term in-situ drug release by mixing the microbubbles and the drug in the temperature-sensitive hydrogel. After treating the drug delivery composition around the affected area, the microbubbles are destructed by ultrasonic treatment before gel-forming. Then, cavitation effect is produced to make the cell membrane of the affected area produce temporary holes, which greatly improved the efficiency of drug entering the affected area. At the same time, when the drug delivery composition of the present disclosure is affected by body temperature, it can be gel-forming and fixed on the affected area or around the affected area, so as to achieve the effect of long-term stable in-situ treatment. Taken together, the drug delivery composition of the present disclosure not only improves the efficiency of drug release efficiency and absorption, but also solves the problem of side effects caused by high-dose treatment on some organs and tissues, and further achieves the effect of in-situ treatment. Furthermore, it is also known from previous examples that the drug delivery composition of the present disclosure has very little side effects on animals, so the future development should be unlimited.

Although the present disclosure has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present disclosure without departing from the scope or spirit of the invention. In view of the foregoing, it is intended that the present disclosure cover modifications and variations of this invention provided they fall within the scope of the following claims.

What is claimed is:

1. A drug delivery composition, comprising:
   a temperature-sensitive hydrogel, wherein the temperature-sensitive hydrogel comprises poloxamer 407, a total weight of the drug delivery composition is 100 percentage by weight, and a content of the poloxamer 407 is no more than 12.5 percentage by weight;
   a plurality of microbubbles, wherein each of the plurality of microbubbles has a protein shell and an inert gas core, and the plurality of microbubbles are dispersed in the temperature-sensitive hydrogel, and an amount of the plurality of microbubbles of the drug delivery composition is from about $1 \times 10^8$ to about $2 \times 10^{10}$ per mL; and
   a drug, dispersed in the temperature-sensitive hydrogel;
   wherein the drug delivery composition has a gel-forming temperature, the gel-forming temperature is greater than 25° C., the drug delivery composition has a viscosity for inducing cavitation effect of ultrasound before gel-forming and forms a fixed gel at a body temperature of a subject, and the viscosity for inducing cavitation effect is from about 0.01 Pa·S to about 1.3846 Pa·S.

2. The drug delivery composition of claim 1, wherein a content of the temperature-sensitive hydrogel is from about 8 percentage by weight, and a content of the plurality of microbubbles is from about 1 percentage by weight to about 10 percentage by weight.

3. The drug delivery composition of claim 1, wherein a particle diameter of each of the plurality of microbubbles is from about 0.5 μm to about 3.7 μm.

4. The drug delivery composition of claim 1, wherein the drug is selected from the group consisting of steroid, anti-apoptotic drug, neurotrophic factor, growth factor, antibiotic, antioxidant, and a combination thereof.

5. A method for treating inner ear disorders, the method comprising administering to a subject in need thereof an effective amount of the drug delivery composition of claim 1.

6. A method of manufacturing a drug delivery composition of claim 1, the method comprising following steps:
   mixing a microbubble material and a first solvent to form a first mixture;
   treating the first mixture with an ultrasonic wave for about 100 seconds to 140 seconds to form a plurality of microbubbles, wherein each of the plurality of microbubbles has a protein shell and an inert gas core;
   mixing a drug and a second solvent to form a second mixture;
   mixing the second mixture and a temperature-sensitive hydrogel to form a temperature-sensitive drug hydrogel, wherein the temperature-sensitive hydrogel comprises poloxamer 407, a total weight of the drug delivery composition is 100 percentage by weight, and a content of the poloxamer 407 is no more than 12.5 percentage by weight; and
   mixing the plurality of microbubbles and the temperature-sensitive drug hydrogel to form the drug delivery composition, wherein the drug delivery composition has a viscosity for inducing cavitation effect, the viscosity for inducing cavitation effect is from about 0.01 Pa·S to about 1.3846 Pa·S, and a gel-forming temperature of the drug delivery composition is greater than 25° C., and an amount of the plurality of microbubbles of the drug delivery composition is from about $1 \times 10^8$ to about $2 \times 10^{10}$ per mL.

7. The method of claim 6, wherein the first solvent comprises saline.

8. The method of claim 6, wherein the second solvent comprises dimethyl sulfoxide.

9. The method of claim 6, wherein a content of the temperature-sensitive hydrogel is from about 8 percentage by weight, and a content of the plurality of microbubbles is from about 1 percentage by weight to about 10 percentage by weight.

10. The method of claim 6, wherein a particle diameter of each of the plurality of microbubbles is from about 0.5 μm to about 3.7 μm.

11. The method of claim 6, wherein the drug is selected from the group consisting of steroid, anti-apoptotic drug, neurotrophic factor, growth factor, antibiotic, antioxidant, and a combination thereof.

12. The drug delivery composition of claim 1, wherein the gel-forming temperature of the drug delivery composition is smaller than 35° C.

13. A drug delivery composition, comprising:
   a temperature-sensitive hydrogel, wherein the temperature-sensitive hydrogel comprises poloxamer 407, a total weight of the drug delivery composition is 100 percentage by weight, and a content of the poloxamer 407 is no more than 12.5 percentage by weight;
   a plurality of microbubbles, wherein each of the plurality of microbubbles has a protein shell and an inert gas core, and the plurality of microbubbles are dispersed in the temperature-sensitive hydrogel, and an amount of the plurality of microbubbles of the drug delivery composition is from about $1\times10^8$ to about $2\times10^{10}$ per mL; and a drug, dispersed in the temperature-sensitive hydrogel;

wherein the drug delivery composition has a viscosity for inducing cavitation effect of ultrasound before gel-forming and forms a fixed gel at a body temperature of a subject, the viscosity increases with increase of temperature, the drug delivery composition has a gel-forming temperature, the gel-forming temperature is greater than 25° C., and at a temperature range of 25° C. to 35° C., the viscosity has a range from 0.8029 Pa·S to 1.3846 Pa·S.

14. The drug delivery composition of claim 1, wherein the content of the poloxamer 407 is more than about 10 percentage by weight.

15. The drug delivery composition of claim 13, wherein a content of the temperature-sensitive hydrogel is from about 8 percentage by weight, and a content of the plurality of microbubbles is from about 1 percentage by weight to about 10 percentage by weight.

16. The drug delivery composition of claim 13, wherein a particle diameter of each of the plurality of microbubbles is from about 0.5 μm to about 3.7 μm.

17. The drug delivery composition of claim 13, wherein the drug is selected from the group consisting of steroid, anti-apoptotic drug, neurotrophic factor, growth factor, antibiotic, antioxidant, and a combination thereof.

18. The drug delivery composition of claim 13, wherein the content of the poloxamer 407 is more than about 10 percentage by weight.

* * * * *